US008173121B2

(12) United States Patent
Li et al.

(10) Patent No.: US 8,173,121 B2
(45) Date of Patent: May 8, 2012

(54) LYSYL OXIDASE-LIKE 1 (LOXL1) AND ELASTOGENESIS

(75) Inventors: Tiansen Li, Quincy, MA (US); Xiaoqing Liu, Weymouth, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 12/699,701

(22) Filed: Feb. 3, 2010

(65) Prior Publication Data

US 2010/0203029 A1 Aug. 12, 2010

Related U.S. Application Data

(62) Division of application No. 11/809,495, filed on Jun. 1, 2007, now Pat. No. 7,674,458, which is a division of application No. 11/041,589, filed on Jan. 24, 2005, now Pat. No. 7,255,856.

(60) Provisional application No. 60/538,962, filed on Jan. 23, 2004.

(51) Int. Cl.
*A61K 38/44* (2006.01)
*A61P 27/02* (2006.01)
*A61P 17/00* (2006.01)
(52) U.S. Cl. .................. 424/94.4; 424/70.1; 514/12.1
(58) Field of Classification Search .................. None
See application file for complete search history.

(56) References Cited

U.S. PATENT DOCUMENTS

| | | | |
|---|---|---|---|
| 5,166,187 | A | 11/1992 | Collombel et al. |
| 6,541,023 | B1 | 4/2003 | Andre et al. |
| 6,790,454 | B1 | 9/2004 | Malak et al. |
| 2002/0150564 | A1 | 10/2002 | Ensley |
| 2004/0002055 | A1 | 1/2004 | Andre et al. |
| 2004/0248811 | A1 | 12/2004 | Hwang et al. |
| 2004/0253220 | A1 | 12/2004 | Perrier et al. |
| 2004/0258676 | A1 | 12/2004 | Perrier et al. |
| 2005/0208478 | A1 | 9/2005 | Andre et al. |

FOREIGN PATENT DOCUMENTS

| | | |
|---|---|---|
| EP | 0 296 078 | 12/1988 |
| EP | 0 374 440 | 6/1990 |
| FR | 2 828 206 | 2/2003 |
| WO | WO 97/48823 | 12/1997 |
| WO | WO 00/44910 | 8/2000 |
| WO | WO 01/83702 | 11/2001 |
| WO | WO 01/91821 | 12/2001 |
| WO | WO 01/92322 | 12/2001 |
| WO | WO 02/11667 | 2/2002 |
| WO | WO 02/061092 | 8/2002 |

OTHER PUBLICATIONS

Bank et al., "Lysyl Oxidase: New looks on LOX," Arteriosclerosis, Thrombosis, and Vascular Biology, 22:1365-1366 (2002).
El Hemaly et al., "Stress urinary incontinence, a new concept," European Journal of Obstetrics & Gynecology and Reproductive Biology, 68:129-135 (1996).
Fornieri et al., "Elastin Production and degradation in Cutis Laxa Aquisita," Journal of Investigative Dermatology, 10:583-588 (1994).
Klein et al., "The association of cardiovascular disease with the long-term incidence of age-related maculopathy: the beaver dam eye study," Ophthalmology, 110:1273-1280 (2003).
Office Action issued in Japanese Patent Application 2006-551342 dated Dec. 15, 2010 (translated).
Okamoto, "Structure and function of elastic fiber," Japanese Journal of Dermatology, 112:1726-1728 (2002) (with partial translation).
Osman et al., "Stimulation of lung lysyl oxidase activity in hamsters with elastase-induced emphysema," The American Review of Respiratory Disease, 131:169-170 (1985).
Wacchi, "Elastic fiber and its abnormality, cutis laxa and elastogeneis," Japanese Journal of Dermatology, 112:1731-1733 (2002) (with partial translation).
Allen et al., "Pelvic floor damage and childbirth: a neurophysiological study," British Journal Obstetrics and Gynaecology, vol. 97, pp. 770-900 (1990).
Ashcroft et al., "Age-related changes in the temporal and spatial distributions of fibrillin and elastin mRNAs and proteins in acute cutaneous wounds of healthy humans," Journal of Pathology, vol. 183, pp. 80-89 (1997).
Boak et al., "Regulation of lysyl oxidase expression in lung fibroblasts by transforming growth factor-β1 and Prostaglandin $E_2$," American Journal of Respiratory Cell and Molecular Biology, vol. 11, pp. 751-755 (1994).
Borel et al., "Lysyl oxidase-like protein from bovine aorta," The Journal of Biological Chemistry, 276(52):48944-48949 (2001).
Brassart et al., "Conformational dependence of collagenase (matrix metalloproteinase-1) up-regulation by elastin peptides in cultured fibroblasts," Journal of Biological Chemistry, vol. 276, No. 7, pp. 5222-5227 (2001).
Bryant-Greenwood and Schwabe, "Human relaxins: chemistry and biology," Endocrine Reviews, vol. 15, No. 1, pp. 5-26 (1994).
Chaudhry et al., "Mutation of the gene encoding fibrillin-2 results in syndactyly in mice," Human Molecular Genetics, vol. 10, No. 8, pp. 835-843 (2001).
Cheater and Castledon, "Epidemiology and classification of urinary incontinence," Clinical Obstetrics and Gynaecology, vol. 14, No. 2, pp. 183-205 (2000).
Counts et al., "Collagen lysyl oxidase activity in the lung increases during bleomycin-induced lung fibrosis," J. Pharmacol. Exp. Ther., 219(3):675-678 (1981).
Csiszar, "Lysal oxidases: a novel multifunctional amine oxidase family," Progress in Nucleic Acid Research and Molecular Biology, Moldave (Ed.) vol. 70, pp. 2-28 (2001).
Decitre et al., "Lysyl oxidase-like protein localizes to sites of de novo fibronogenesis in fibrosis and in the early stromal reaction of ductal breast carcinomas," Laboratory Investigation, vol. 78, No. 2, pp. 143-151 (1998).
Di Donato et al., "Lysyl oxidase expression and collagen cross-linking during chronic adriamycin nephropathy," Nephron., 76(2):192-200 (1997).
Diokno et al., "Epidemiology of bladder emptying symptoms in elderly men," Journal of Urology, vol. 148, pp. 1817-1821 (1992).
Duplan-Perrat, "Keratinocytes influence the maturation and organization of the elastin network in a skin equivalent," The Journal of Investigative Dermatology, vol. 114, No. 2, pp. 365-370 (2000).

(Continued)

Primary Examiner — Kagnew H Gebreyesus
(74) Attorney, Agent, or Firm — Fish & Richardson P.C.

(57) ABSTRACT

Described are methods of treating and preventing conditions associated with a loss of elastic fibers. Also provided herein are methods of screening for agents useful in treating such conditions, and animal models of conditions associated with a loss of elastic fibers.

43 Claims, 5 Drawing Sheets

OTHER PUBLICATIONS

Hafezi-Moghadam et al., "A novel mouse-driven ex vivo flow chamber for the study of leukocyte and platelet function," *American Journal of Cell Physiology*, vol. 286, pp. 876-892 (2004).
Hautamaki et al., "Requirement for macrophage elastase for cigarette smoke-induced emphysema in mice," *Science*, vol. 277, pp. 2002-2004 (1997).
Hinek and Rabinovitch, "67-kD Elastin-binding protein is a protective 'companion' of extracellular insoluble elastin and intracellular tropoelastin," *Journal of Cell Biology*, vol. 126, No. 2, pp. 563-574 (1994).
Hong et al., "Retinitis pigmentosa GTPase Regulator (RPGR)-interacting protein is stably associated with the photoreceptor ciliary axoneme and anchors RPGR to the connecting cilium," *Journal of Biological Chemistry*, vol. 276, No. 15, pp. 12091-12099 (2001).
Hornstra et al., "Lysyl oxidase is required for vascular and diaphragmatic development in mice," Journal of Biological Chemistry, 278(16):14387-14393 (2003).
Jeay et al., "Lysyl oxidase inhibits ras-mediated transformation by preventing activating of NF-κB," Molecular and Cellular Biology, 23(7):2251-2263 (2003).
Kagan et al., "Control of elastin metabolism by elastin ligands," *The Journal of Biological Chemistry*, vol. 256, No. 11, pp. 5417-5421 (1981).
Kagan et al., "Lysyl oxidase: properties, specificity, and biological roles inside and outside of the cell," *Journal of Cellular Biochemistry*, vol. 88, pp. 660-672 (2003).
Kagan et al., "Ultrastructural immunolocalization of lysyl oxidase in vascular connective tissue," *Journal of Cell Biology*, vol. 103, pp. 1121-1128 (1986).
Kagan, "Intra- and extracellular enzymes of collagen biosynthesis as biological and chemical targets in the control of fibrosis," *Acta Tropica*, vol. 77, pp. 147-152 (2000).
Karnik et al., "A critical role for elastin signaling in vascular morphogenesis and disease," *Development and Disease*, vol. 130, pp. 411-423 (2003).
Keane and O'Sullivan, "Urinary incontinence: anatomy, physiology and pathophysiology," *Baillières Clinical Obstetrics and Gynaecology*, vol. 14, No. 2, pp. 207-226 (2000).
Kelly and Dumm, "Urinary incontinence in women, without manifest injury to the bladder," *Surgery, Gynecology and Obstetrics*, vol. 18, pp. 444-450 (1914).
Kenyon et al., "A novel human cDNA with a predicted protein similar to lysyl oxidase maps to chromosome 15q24-q25," *The Journal of Biological Chemistry*, vol. 268, No. 25, pp. 18435-18437 (1993).
Kielty et al., "Elastic fibres," *Journal of Cell Science*, vol. 115, pp. 2817-2828 (2002).
Kim et al., "A new gene with sequence and structural similarity to the gene encoding human lysyl oxidase," J. Biol. Chem., 270(13):7176-7182 (1995).
Kim et al., "Coexpression of the lysyl oxidase-like gene (LOXL) and the gene encoding type III procollagen in induced liver fibrosis," J. Cell Biochem., 72(2):181-188 (1999).
Kirschmann et al., "A molecular role for lysyl oxidase in breast cancer invasion," *Cancer Research*, vol. 62, pp. 4478-4483 (2002).
Koduri and Sand, "Recent developments in pelvic organ prolapse," *Current Opinion in Obstetrics and Gynecology*, vol. 12, No. 5, pp. 399-404 (2000).
Krege et al., "A noninvasive computerized tail-cuff system for measuring blood pressure in mice," *Hypertension*, vol. 25, pp. 1111-1115 (1995).
La Fontaine et al., "Intracellular localization and loss of copper responsiveness of Mnk, the murine homologue of the Menkes protein, in cells from blotchy (Mo blo) and brindled (Mo br) mouse mutants," Hum. Mol. Genet., 8(6):1069-1075 (1999).
Leppert, "Anatomy and physiology of cervical ripening," *Clinical Obstetrics and Gynecology*, vol. 38, No. 2, pp. 267-279 (1995).
Liu et al., "Elastic fiber homeostasis requires lysyl oxidase-like 1 protein," *Nature Genetics*, vol. 36, No. 2, pp. 178-182 (2004).
Mäki et al., "Inactivation of the lysyl oxidase gene *lox* leads to aortic aneurysms, cardiovascular dysfunction and perinatal death in mice," Circulation, 106:2503-2509 (2002).

Mäki, "Lysyl oxidases: cloning and characterization of the fourth and the fifth human lysyl oxidase isoenzymes, and the consequences of a targeted inactivation of the first described lysyl oxidase isoenzyme in mice," *Collagen Research Unit, Biocenter Oulu and Department of Medical Biochemistry and Molecular Biology, University of Oulu* (2002).
Mäkinen et al., "Transdermal estrogen for female stress urinary incontinence in postmenopause," *Maturitas*, vol. 22, pp. 233-238 (1995).
Mann et al., "Copper metabolism in mottled mouse (*Mus musculus*) mutants. Studies of blotchy (Moblo) mice and a comparison with brindled (Mobr) mice," Biochem. J. 196(1):81-88 (1981).
Mecham and Davis, "Elastic fiber structure and assembly," In: Yurchenco, *Extracellular Matrix Assembly and Structure*, pp. 281-314 (1994).
Michel et al., "Characterization of a new tissue-engineered human skin equivalent with hair," In Vitro Animal, 35(6):318-326 (1999).
Mochizuki et al., "Signaling pathways transduced through the elastin receptor facilitate proliferation of arterial smooth muscle cells," *Journal of Biological Chemistry*, vol. 277, No. 47, pp. 44854-44863 (2002).
Molnar et al., "Structural and functional diversity of lysyl oxidase and the LOX-like proteins," *Biochimica et Biophysica Acta*, vol. 1647, No. 1, pp. 220-224 (2003).
Morris et al., "Loss of integrin αvβ6-mediated TGF-β activation causes mmp12-dependant emphysema," *Nature*, vol. 422, 169-173 (2003).
Nakamura et al., "Fibulin-5/DANCE is essential for elastogenesis in vivo," Nature, 415:171-175 (2002).
Niewoehner et al., "Lung fibrosis and emphysema: divergent responses to a common injury?" Science, 217(4557):359-360 (1982).
Noblesse et al., "Lysyl oxidase-like and lysyl oxidase are present in the dermis and epidermis of a skin equivalent and in human skin and are associated to elastic fibers," The Society of Investigative Dermatology, 122:621-630 (2004).
Olsen et al., "Epidemiology of Surgically Managed Pelvic Organ Prolapse and Urinary Incontinence," *Obstetrics & Gynecology*, vol. 89, No. 4, pp. 501-506 (1997).
Palamakumbura and Trackman, "A fluorometric assay for detection of lysyl oxidase enzyme activity in biological samples," *Analytical Biochemistry*, vol. 300, pp. 245-251 (2002).
Pasquali-Ronchetti and Baccarani-Contri, "Elastic fiber during development and aging," *Microscopy Research and Technique*, vol. 38, pp. 428-435 (1997).
Pereira et al., "Targetting of the gene encoding fibrillin-1 recapitulates the vascular aspect of Marfan syndrome," Nature Genetics, 17:218-222 (1997).
Rechberger et al., "Female urinary stress incontinence in terms of connective tissue biochemistry," *European Journal of Obstetrics & Gynecology and Reproductive Biology*, vol. 49, pp. 187-191 (1993).
Resnick, "Improving treatment of urinary incontinence," *JAMA*, vol. 280, No. 23, pp. 2034-2035 (1998).
Retzky and Rogers, "Urinary incontinence in women," *Clinical Symposia*, vol. 47, No. 3, pp. 2-32 (1995).
Romanzi et al., "The effect of genital prolapse on voiding," J. Urology, 161:581-586 (1999).
Romanzi, "Urinary incontinence in women and men," *The Journal of General-Specific Medicine*, vol. 4, No. 3, pp. 14-20 (2001).
Saito et al., "Regulation of a novel gene encoding a lysyl oxidase-related protein in cellular adhesion and senescence," The Journal of Biological Chemistry, 272(13):8157-8160 (1997).
Seve et al., "Expression analysis of recombinant lysyl oxidase (LOX) in myofibroblastlike cells," Connective Tissue Research, 43:613-619 (2002).
Shapiro, "The pathogenesis of emphysema: the elastase: antielastase hypothesis 30 years later," Proceedings of the Association of American Physicians, 107(3):346-352 (1995).
Silver et al., "Viscoelasticity of the vessel wall: the role of collagen and elastic fibers," *Critical Reviews in Biomedical Engineering*, vol. 29, No. 3, pp. 279-302 (2001).
Smith-Mungo and Kagan, "Lysyl oxidase: properties, regulation and multiple functions in biology," *Matrix Biology*, vol. 16, pp. 387-398 (1998).

Snooks et al., "Effect of vaginal delivery on the pelvic floor: a 5-year follow-up," *The British Journal of Surgery*, vol. 77, No. 12, pp. 1358-1360 (1990).

Snooks et al., "Risk factors in childbirth causing damage to the pelvic floor innervation," *International Journal of Colorectal Disease*, vol. 1, No. 1, pp. 20-24 (1986).

Starcher and Percival, "Elastin turnover in the rat uterus," *Connective Tissue Research*, vol. 13, No. 3, pp. 207-215 (1985).

Starcher et al., "Abnormal cellular copper metabolism in the blotchy mouse," J. Nutr. 108(8):1229-1233 (1978).

Starcher et al., "Lysyl oxidase deficiency in lung and fibroblasts from mice with hereditary emphysema," Biochem. Biophys. Res. Commun., 78(2):706-712 (1977).

Sultan et al., "The pelvic floor sequelae of childbirth," British Journal of Hospital Medicine, 55(9):575-579 (1996).

Thomas et al., "Prevalence of urinary incontinence," *British Medical Journal*, vol. 281, pp. 1243-1245 (1980).

Thomassin et al., "The Pro-regions of Lysyl Oxidase and Lysyl Oxidase-like 1 Are Required for Deposition onto Elastic Fibers," J. Biol. Chem., 280(52):42848-42855, (2005).

Turan et al., "Urinary incontinence in women of reproductive age," *Gynecologic and Obstetric Investigation*, vol. 41, pp. 132-134 (1996).

Ulmsten and Falconer, "Connective tissue in female incontinence," *Current Opinion in Obstetrics and Gynecology*, vol. 11, No. 5, pp. 509-515 (1999).

Vikrup and Lose, "Lower urinary tract symptoms 5 years after the first delivery," *International Urogynecology Journal*, vol. 11, pp. 336-340 (2000).

Vrhovski and Weiss, "Biochemistry of tropoelastin," *European Journal of Biochemistry*, vol. 258, pp. 1-18 (1998).

Wachi et al., "Endothelin-1 down-regulates expression of tropoelastin and lysyl oxidase mRNA in cultured chick aortic smooth muscle cells," *Journal of Health Science*, vol. 47, No. 6, pp. 525-532 (2001).

Watson et al., "Fibrillin- rich microfibrils are reduced in photoaged skin. Distribution at the dermal-epidermal junction," *The Journal of Investigative Dermatology*, vol. 112, No. 5, pp. 782-787 (1999).

Woessner and Brewer, "Formation and breakdown of collagen and elastin in the human uterus during pregnancy and post-partum involution," *The Biochemical Journal*, vol. 89, pp. 75-82 (1963).

Yamamoto et al., "Changes in elastin-binding protein in fibroblasts derived from cardinal ligaments of patients with prolapsus uteri," *Cell Biology International*, vol. 26, No. 5, pp. 441-449 (2002).

Yanagisawa et al., "Fibulin-5 is an elastin-binding protein essential for elastic fibre development in vivo," *Nature*, vol. 415, pp. 168-171 (2002).

FIG. 1A
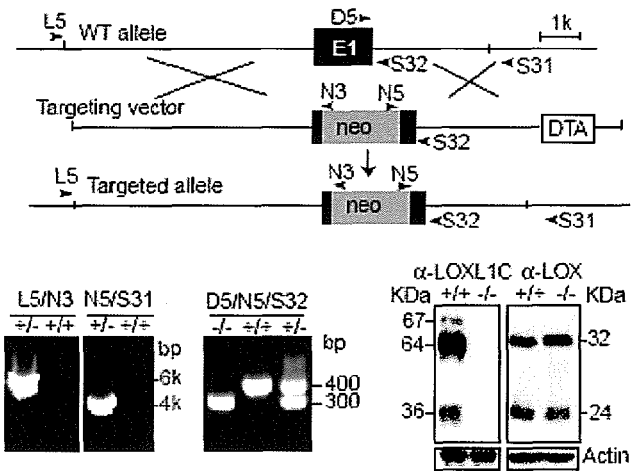
FIG. 1B          FIG. 1C
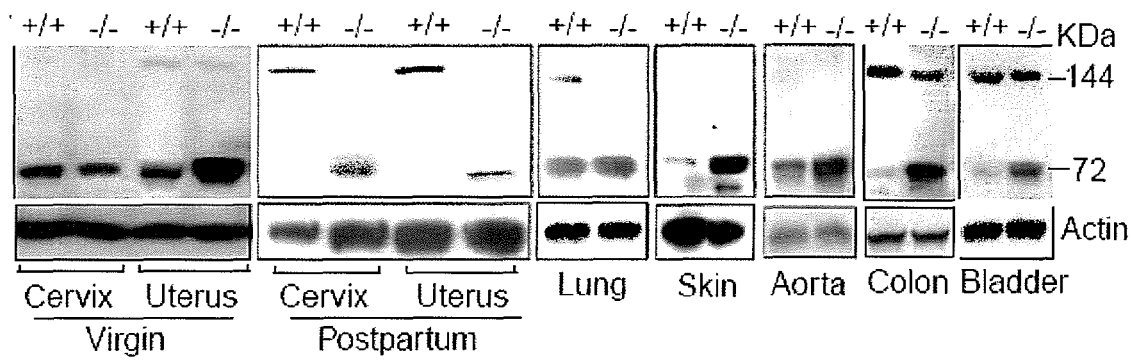
FIG. 2A
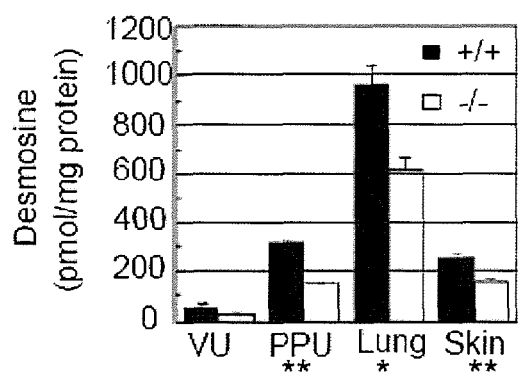
FIG. 2B
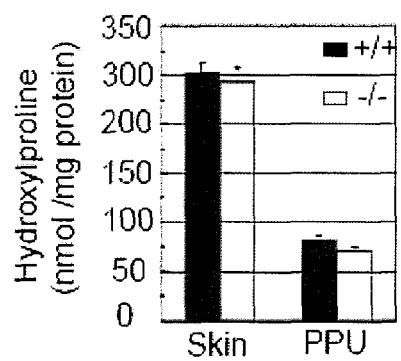
FIG. 2C

LYSYL OXIDASE-LIKE 1 (LOXL1) AND ELASTOGENESIS

CLAIM OF PRIORITY

This application is a divisional of U.S. patent application Ser. No. 11/809,495, filed on Jun. 1, 2007, now U.S. Pat. No. 7,674,458, which is a divisional of U.S. patent application Ser. No. 11/041,589, filed on Jan. 24, 2005, now U.S. Pat. No. 7,255,856, issued Aug. 14, 2007, which claims the benefit of U.S. Provisional Patent Application Ser. No. 60/538,962, filed on Jan. 23, 2004, the entire contents of which are hereby incorporated by reference.

BACKGROUND

The major component of elastic fibers is an amorphous polymer composed of the polypeptide elastin (known as tropoelastin when in monomeric form). Polymerization of elastic fibers requires an initial step of oxidative deamination of lysine residues, which is catalyzed by a lysyl oxidase (Kagan et al., *J. Cell. Biochem.* 88, 660-672 (2003)). The resulting aldehyde groups condense spontaneously with adjacent aldehydes or ε-amino groups of peptidyl lysine to form covalent cross-linkages. Lysyl oxidases are copper-dependent monoamine oxidases secreted by fibrogenic cells including fibroblasts and smooth muscle cells. Mammalian genomes have up to five potential LOX family members coding for the prototypic LOX and LOX-like polypeptides 1 through 4 (LOXL1-4) (Kagan et al., supra). Their individual roles in elastogenesis was unclear.

Elastogenesis also requires a scaffolding structure onto which elastin is deposited. Microfibrils, made up of fibrillins and microfibril-associated glycoproteins, are thought to serve as a scaffold which guides elastin deposition (Kielty et al., *J. Cell. Sci.* 115, 2817-2828 (2002)). However, inactivation of fibrillin 1 and 2 genes individually suggests that each is dispensable for elastogenesis (Pereira et al., *Nat. Genet.* 17, 218-222 (1997); Chaudhry et al., *Hum. Mol. Genet.* 10, 835-843 (2001)). Elastin binding protein (EBP) (Hinek et al., *J. Cell. Biol.* 126, 563-574 (1994)), fibulin-5 (Yanagisawa et al., *Nature* 415, 168-171 (2002)) and an unspecified lysyl oxidase (Kagan et al., *J. Cell. Biol.* 103, 1121-1128 (1986)) were also reported to associate with elastic fibers. Gene targeting studies show that fibulin-5 is required for elastic fiber development (Yanagisawa et al., *Nature* 415, 168-171 (2002); Nakamura et al., *Nature* 415, 171-175 (2002)). Disruption of the Lox gene leads to a reduction in collagen and elastin cross-links and perinatal lethality (Maki et al., *Circulation* 106, 2503-2509 (2002); Hornstra et al., *J. Biol. Chem.* 278, 14387-14393 (2003)), suggesting a role in cross-linking both fibrillar collagens and elastin during development.

SUMMARY

The present invention is based, in part, on the discovery that Lysyl Oxidase-Like 1 (LOXL1) has a generalized, non-redundant role in elastic fiber homeostasis in adult tissues. As described herein, LOXL1 is essential for elastic fiber remodeling and replenishment in all adult tissues. Because of its unique physiology, pelvic organ damage and prolapse are prominent aspects of the disease phenotype among female knockout mice lacking LOXL1, exhibited soon after giving birth. Further, the failure to deposit elastin polymers in the uterine tract post partum is a direct cause of urinary incontinence. In other tissues such as skin, lung, vasculature and connective tissues in general, an insufficiency of LOXL1 leads to a gradual depletion of functional elastic fibers, due to the lack of continued, orderly deposition of polymerized elastin. Thus, the invention provides methods of treating and preventing conditions associated with a loss of elastic fibers by administering compounds that increase LOXL1 activity, i.e., LOXL1 enhancers. For example, to increase endogenous expression, transcriptional activators or the delivery of gene expression constructs through viral or non-viral gene-transfer vectors can be used. Alternatively, LOXL1 polypeptides, or active fragments thereof, can be synthesized in vitro, purified and delivered as a medicine to sites or tissues where it will likely be therapeutic. Thirdly, small molecule or other therapeutic compounds can be administered to boost the enzymatic activity of existing LOXL1.

The invention further provides animal models of conditions associated with a loss of elastic fibers, e.g., LOXL1 transgenic or knockout mice. Also provided herein are methods of screening for agents useful in treating and preventing such conditions.

In one aspect, the invention provides methods for treating a subject having a condition associated with a loss of elastic fibers. The methods include administering to the subject a therapeutically effective amount of a LOXL1 enhancer.

In another aspect, the invention provides methods for preventing the development or progression of a condition associated with a loss of elastic fibers. The methods include administering to the subject a therapeutically effective amount of a LOXL1 enhancer.

In some embodiments, the LOXL1 enhancer is a LOXL1 polypeptide or active fragment thereof, or a nucleic acid encoding a LOXL1 polypeptide or active fragment thereof. In some embodiments, the LOXL1 enhancer is a small molecule or other therapeutic compound, e.g., identified by a method described herein.

In another aspect the invention provides methods for identifying a LOXL1 enhancer. The methods include providing a sample comprising a functional LOXL1, e.g., a LOXL1 polypeptide or nucleic acid; contacting the sample with a test compound, thereby forming a test sample; and measuring an activity of the LOXL1 in the test sample. An increase in LOXL1 activity in the presence of the test compound, as compared to a reference, indicates that the test compound is a LOXL1 enhancer. In some embodiments, the test compound causes an increase in LOXL1 activity by increasing levels of LOXL1 polypeptide, e.g., by increasing LOXL1 transcription, translation, or processing, or by reducing LOXL1 degradation.

In another aspect the invention provides a non-human transgenic mammal, whose cells comprise at least one LOXL1 transgene. In some embodiments, the animal lacks at least one functional LOXL1 allele, e.g., at least one LOXL1 allele produces a non-functional LOXL1 polypeptide, does not produce any LOXL1 polypeptide, or produces a mutant LOXL1 polypeptide that lacks one or more LOXL1 activity as described herein. In some embodiments, the animal lacks both functional LOXL1 alleles. In some embodiments, the animal exhibits one or more symptoms of a condition associated with a loss of elastic fibers. In some embodiments, the animal has a loss of elastic fibers, e.g., in the pelvic organs, skin, eyes, or vascular system. In some embodiments, the animal exhibits at least one symptom of a condition associated with a loss of elastic fibers.

In another aspect the invention provides a non-human animal model of a condition associated with the loss of elastic fibers comprising a transgenic animal whose cells comprise at least one LOXL1 transgene. In some embodiments, the cells of the animal model lack at least one LOXL1 functional allele, e.g., at least one LOXL1 allele produces a non-functional LOXL1 polypeptide, does not produce any LOXL1 polypeptide, or produces a mutant LOXL1 polypeptide that lacks one or more LOXL1 activity as described herein. In some embodiments, the cells of the animal model lack both functional LOXL1 alleles.

In another aspect the invention provides a method of identifying candidate therapeutic compounds (e.g., LOXL1 enhancers) to treat a condition associated with the loss of elastic fibers. The method includes providing a non-human animal model of the condition, wherein the cells of the model animal comprise at least one LOXL1 transgene; administering a test compound to the model animal; and monitoring a parameter associated with the condition. A test compound that positively affects the parameter associated with the condition is a candidate therapeutic compound. A positive affect on a parameter is an improvement in one or more symptoms or other clinical indices associated with the condition.

In some embodiments, a condition associated with a loss of elastic fiber is the loss of skin elasticity (e.g., wrinkly and/or loose skin, such as that associated with normal (e.g., non-pathological) aging or accelerated aging, weight loss, or pregnancy) chronic obstructive pulmonary disease ("COPD"; e.g., emphysema, asthma, or chronic bronchitis), pelvic organ prolapse and urinary incontinence (common in elderly and multiparous women), vascular disease (including aortic dissection, aneurisms, systolic high blood pressure, e.g., hypertension, and stroke), or degradation of the elastic lamina of the Bruch's membrane in the eye that contributes to choroidal neovascularization in age-related macular degeneration. "A loss of elastic fibers" includes both a partial loss of elastic fibers and/or a complete or substantially complete loss of elastic fibers. In some embodiments, a loss of elastic fibers includes a reduction of at least about 40% of elastin crosslinks, as measured by desmosine content. In some embodiments, a loss of elastic fibers includes a reduction of about 50%, 60%, 70%, 80%, 90%, or more in elastin crosslinks, as measured by desmosine content.

A "polypeptide" means a chain of amino acids regardless of length or post-translational modifications. A polypeptide can include full-length, mature and active proteins, precursors, and active fragments comprising amino acid sequences sufficiently identical to (at least 80% identical to) or derived from the amino acid sequence of LOXL1. As used herein, LOXL1 or Lysyl Oxidase-Like-1 polypeptide refers to mammalian LOXL1. Exemplary LOXL1 polypeptide sequences include Genbank Accession number AAH37999 (*mus musculus*); AAH03973 (*mus musculus*); NP_776808 (*bos taurus*); AAH15090 (*homo sapiens*), and homologs thereof. A LOXL1 polypeptide can also be a polypeptide encoded by a LOXL1 nucleic acid. LOXL1 nucleic acids include Genbank Accession Nos. BC037999 and BC003973 (*mus musculus*); BC015090 and NM_002317 (*homo sapiens*); and NM_174383 and AF421185 (*bos taurus*), and homologs thereof.

A "biologically active fragment" of a LOXL1 polypeptide includes a fragment of a LOXL1 polypeptide that has at least one activity of the full-length polypeptide, e.g., participates in an interaction between a LOXL1 molecule and a non-LOXL1 molecule (e.g., a molecule that is a binding partner, e.g., fibulin-5 or tropoelastin), and/or can catalyze the crosslinking of elastin. Biologically active fragments of a LOXL1 polypeptide include peptides comprising amino acid sequences sufficiently homologous to (in some embodiments, at least 80%, 90%, 95% identical to) or derived from the amino acid sequence of a LOXL1 polypeptide (e.g., the amino acid sequence of Genbank Accession number AAH37999 (*mus musculus*); AAH03973 (*mus musculus*); NP_776808 (*bos taurus*); or AAH15090 (*homo sapiens*)) that include fewer amino acids than the full-length LOXL1 polypeptide, and exhibit at least one activity of a LOXL1 polypeptide.

"Subject," as used herein, refers to a mammal, e.g., a human, or an experimental animal model (e.g., a disease model). The subject can be a non-human animal, e.g., a mouse, rat, cat, dog, guinea pig, horse, cow, pig, goat, or other domestic animal.

"Specifically binds" refers to a molecule that binds to a particular entity in a sample, e.g., a specific LOXL1 polypeptide, but that does not substantially recognize or bind to other molecules in the sample, e.g., another type of lysyl oxidase or a non-LOXL1 polypeptide.

The methods described herein can provide an alternative or supplement to surgical methods of treatment of conditions associated with a loss of elastic fibers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1A is a schematic illustrating a strategy for targeted disruption of LOXL1 in mice, as described herein. The targeted allele harbors a deletion of exon 1 that removes the translational initiation codon.

FIG. 1B is a pair of gel photographs identifying targeted ES clones (left) and mouse genotyping (right) by PCR with the indicated primers.

FIG. 1C is a set of immunoblots of adult aorta extracts, showing complete ablation of LOXL1 expression in the mutant animals. Three LOXL1 variant polypeptides are seen: a 64 kDa matching the predicted full-length form absent the secretory signal peptide, a 67 kDa band presumed to be the full-length form with the signal peptide, and a 36 kDa band matching the cleavage product retaining the C-terminal conserved domain (Borel et al., *J. Biol. Chem.* 276, 48944-48949 (2001)). Two LOX variants (24 kDa and 32 kDa) are detected in adult aorta.

FIG. 2A is a set of immunoblots of total tissue homogenates from various tissues, detected by an elastin antibody. 72 kDa, elastin monomer (tropoelastin); 144 kDa, elastin dimer. Mice shown in all panels were between 3 and 5 months of age.

FIGS. 2B and 2C are bar graphs quantifying expression of desmosine (2B) and hydroxyproline (2C). Values shown are means±s.d. Asterisk, $p<0.05$; double asterisk, $p<0.001$.

FIG. 4A is a representative agarose gel analysis of the PCR products. FIG. 4B is a line graph illustrating the changes in LOXL1 expression. Vertical axis shows arbitrary units with the level in non-pregnant female (N) set as 1.0. Values are the averages of three independent samples. GAPDH levels were used as internal normalization standards. Elastin and LOX mRNAs were unchanged through this period. Cr, gestational days; PP, postpartum days.

DETAILED DESCRIPTION

Figure 3A:
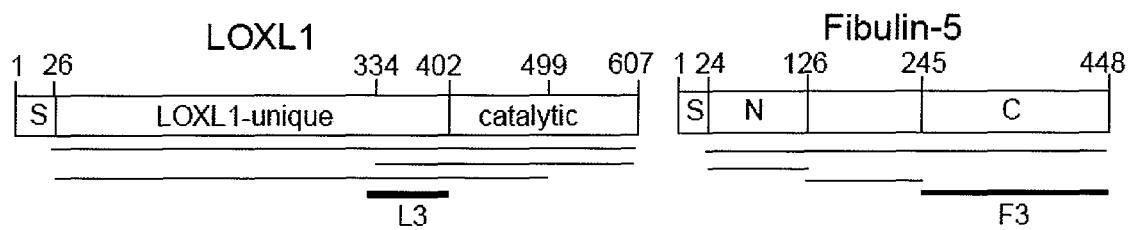
FIG. 3A is a schematic illustration of constructs used in a protein interaction screen using yeast two-hybrid analyses of in vitro and in vivo interactions between mouse LOXL1 (Genbank Accession number AAH37999) and fibulin-5 (Genbank Accession number NP_035942). The maximal interaction domains reside within L3 and F3 regions. S, secretory signal sequence.

The data provided herein demonstrate that Lysyl oxidase-like 1 (LOXL1) has a generalized, non-redundant role for elastic fiber homeostasis in adult tissues. As described herein, LOXL1 is a key positive regulator of elastic fiber formation in adult tissues. The enhancement of LOXL1 function, by administration of a LOXL1 enhancer (e.g., administration of a compound identified by a method described herein, supplementation with exogenous LOXL1, or enhancing synthesis of endogenous LOXL1), is a therapeutic strategy, useful in conditions associated with a loss of elastic fibers. These conditions include the loss of skin elasticity (i.e., wrinkly and loose skin), chronic obstructive pulmonary disease (COPD; e.g., emphysema), pelvic organ prolapse and urinary incontinence (common in elderly and multiparous women), and vascular diseases (including aortic dissection, aneurisms, systolic high blood pressure, and stroke), and degradation of the elastic lamina of the Bruch's membrane in the eye, which contributes to choroidal neovascularization in age-related macular degeneration.

The data described herein also reveal an unexpected, causal link between elastic fiber homeostasis and pelvic prolapse in mice that lack functional LOXL1, a clinical condition strongly correlated with both childbirth and advanced age (Koduri et al., Curr. Opin. Obstet. Gynecol. 12, 399-404 (2000); Sultan et al., Br. J. Hosp. Med. 55, 575-579 (1996); Snooks et al., Br. J. Surg. 77, 1358-1360 (1990)). Elastin polymer and soluble elastin-derived peptides also have signaling roles in cell adhesion, migration and proliferation (Mochizuki et al., J. Biol. Chem. 277, 44854-44863 (2002); Karnik et al., Development 130, 411-423 (2003)). Thus, the combination of the loss of elastin polymer and the accumulation of tropoelastin can contribute to histopathologic changes seen in LOXL1 knockout mice. Genetic defects in human LOXL1 may lead to clinical syndromes resembling generalized elastolysis affecting skin, lung, large arteries and other organs (e.g., cutis laxa type I; OMIM 219100).

Diseases characterized by loss of elastic fibers, such as emphysema, are usually viewed in terms of an imbalance between elastases and their inhibitors (Shapiro et al., Proc. Assoc. Am. Physicians 107, 346-352 (1995); Hautamaki et al., Science 277, 2002-2004 (1997); Morris et al., Nature 422, 169-173 (2003)). The present finding that LOXL1-dependent elastin polymer deposition has an active role in elastic fiber homeostasis shows that an imbalance between degradation and renewal can play a role in such disorders. Thus, LOXL1 is a therapeutic target that is affected by factors that promote elastic fiber loss. For example, smoking lowers copper content in the lung. As copper is required for LOXL1 function, this could in turn lower LOXL1 activity, inhibit renewal, and promotes net loss of elastic fibers and subsequent pathogenesis.

Transgenic Animals

Described herein are non-human transgenic animals. Such animals are useful as models of conditions associated with the loss of in elastic fibers. Such conditions include clinical syndromes resembling generalized elastolysis affecting skin, lung, large arteries and other organs. These conditions include: the loss of skin elasticity (i.e., wrinkly and loose skin), chronic obstructive pulmonary disease (COPD; e.g., emphysema), pelvic organ prolapse and urinary incontinence (common in elderly and multiparous women), and vascular diseases (including aortic dissection, aneurisms, systolic high blood pressure, and stroke), and degradation of the elastic lamina of the Bruch's membrane in the eye that contributes to choroidal neovascularization in age-related macular degeneration. As used herein, a "transgenic animal" is a non-human animal, e.g., a mammal, such as a rodent (e.g., a rat or mouse), in which one or more of the cells of the animal includes a LOXL1 transgene. Other examples of transgenic animals include non-human primates, sheep, dogs, cows, goats, chickens, amphibians, and the like. In some embodiments, the transgenic animals exhibit a loss of elastic fibers.

A transgene is exogenous DNA or a rearrangement, e.g., a deletion, of endogenous chromosomal DNA, which typically is integrated into or occurs in the genome of the cells of a transgenic animal. A transgene can direct (e.g., reduce or eliminate) the expression of an encoded polypeptide in one or more cell types or tissues of the transgenic animal, other transgenes, e.g., a knockout, reduce expression. Thus, a transgenic animal can be one in which an endogenous LOXL1 gene has been altered by, e.g., by homologous recombination between an endogenous gene and an exogenous DNA molecule introduced into a cell of the animal, e.g., an embryonic cell of the animal, prior to development of the animal. In some embodiments, the invention includes transgenic animals lacking one or more functional LOXL1 alleles, e.g., heterozygous or homozygous LOXL1 knockout animals that do not express a functional LOXL1 polypeptide from one or both genes. A functional LOXL1 polypeptide has full LOXL1 activity and is capable of catalyzing the crosslinking of elastin.

The invention also includes targeting vectors useful in creating transgenic animals, as described herein, e.g., targeting vectors that ablate all or part of an allele of the LOXL1 gene such that the remaining sequence does not produce a functional LOXL1 polypeptide. In some embodiments, the vector comprises a replacement gene knockout construct which leads to the deletion of a portion of the coding region, e.g., exon 1. In some embodiments, the vector includes a non-constitutive promoter, e.g., a conditional promoter that allows controlled ablation of the LOXL1 gene.

Intronic sequences and polyadenylation signals can also be included in the transgene to increase the efficiency of expression of the transgene. A tissue-specific regulatory sequence(s) can be operably linked to a transgene of the invention to direct expression of a LOXL1 polypeptide to particular cells. A transgenic founder animal can be identified based upon the presence of a LOXL1 transgene in its genome and/or expression of LOXL1 mRNA in tissues or cells of the animals. A transgenic founder animal can then be used to breed additional animals carrying the transgene. Moreover, transgenic animals carrying a transgene encoding a LOXL1 polypeptide can further be bred to other transgenic animals carrying other transgenes.

LOXL1 polypeptides can be expressed in transgenic animals or plants, e.g., a nucleic acid encoding the polypeptide can be introduced into the genome of an animal. In some embodiments the nucleic acid is placed under the control of a tissue specific promoter, e.g., a milk or egg specific promoter, and the LOXL1 polypeptide is recovered from the milk or eggs produced by the animal. Suitable animals are mice, pigs, cows, goats, and sheep.

Methods of Diagnosis—Detection of LOXL1

LOXL1 can be detected in cells and tissues using methods known in the art, e.g., using anti-LOXL1 antibodies and/or nucleic acid probes. As described herein, a decrease in LOXL1 mRNA expression is associated with a loss of elastic fibers (and conditions associated therewith). Therefore, detection of LOXL1, and detection of decreases in LOXL1 expression, has diagnostic value in both clinical and academic settings. Detection of LOXL1 mRNA levels, e.g., by PCR, or polypeptide levels, e.g., by immunodetection, in normal and pathological tissue specimens can identify tissues that are undergoing, or at risk for undergoing, a loss of elastic fibers.

Thus the present invention provides diagnostic methods for conditions associated with a loss of, or decline in, elastic fibers. The methods include detecting the presence and/or levels of LOXL1. The methods can include: providing a sample from a subject, contacting the sample with a LOXL1 probe (e.g., anti-LOXL1 antibody, nucleic acid probe or other LOXL1-specific binding moiety); and detecting the probe in the sample, e.g., binding of the probe to a LOXL1 mRNA or polypeptide. The detecting can include determining location or time of formation of the binding, and can include determining the levels of LOXL1 mRNA or polypeptide present in the sample. A difference, e.g., a statistically significant change or difference, in the levels of the LOXL1 mRNA or polypeptide in the sample relative to a reference sample can be an indicator that the subject from whom the sample was obtained has, or is at risk for having, a condition associated with decreased LOXL1 levels, i.e., a condition associated with a loss of, or a decline in, elastic fibers as described herein. In some embodiments, a reference is a control, e.g., a positive or negative control, e.g., a reference sample. In some embodiments, the reference is from a pathological sample, e.g., is representative of results obtained in a given stage of a disease or condition. In some embodiments, LOXL1 is evaluated by immunostaining a skin biopsy sample; normally LOXL1 exists in a strong fibrillar pattern. The absence of a strong fibrillar pattern is indicative of the presence of a LOXL1 related condition.

A LOXL1 probe can include a label, e.g., a directly or indirectly detectable substance. Suitable detectable substances include various enzymes, prosthetic groups, fluorescent materials, luminescent materials and radioactive materials, e.g., as known in the art and described herein. In some embodiments of the invention, a labeled LOXL1 probe such as a LOXL1 specific antibody (e.g., as described herein), binding moiety, or nucleic acid that specifically binds to LOXL1, a fragment thereof, or to a LOXL1 nucleic acid (e.g., gene or mRNA) is used for detecting LOXL1, as described herein. For example, LOXL1 can be detected using a DNA binding assay such as those known in the art and described herein (see, e.g., van Wijnen et al., *Mol. Cell. Biol.* 12, 3273-3287 (1992), and van Wijnen et al., *J. Cell. Biochem.* 46, 174-189 (1991)).

Methods of Treatment and Prevention

In some embodiments the invention includes both prophylactic and therapeutic methods of treating a subject at risk of (i.e., susceptible to) or having a disorder, associated with a decrease in LOXL1 expression or activity. This includes a subject at risk of or having a condition characterized by a loss of, or decrease in, elastic fibers, as described herein.

In one aspect, the invention includes a method for treating or preventing a condition associated with a loss of LOXL1 expression or activity in a subject (i.e., a condition characterized by a loss of elastic fibers, as described herein), by administering to the subject a LOXL1 enhancer, e.g., LOXL1 (e.g., a LOXL1 polypeptide, or active fragment thereof, or a nucleic acid encoding LOXL1 polypeptide or active fragment thereof), or another agent that modulates (i.e., increases) LOXL1 expression or at least one LOXL1 activity. Subjects at risk for a condition that is caused or contributed to by a decrease in or loss of LOXL1 expression or activity can be identified by, for example, any one or a combination of the assays described herein for measuring LOXL1 expression or activity, or by diagnosing a condition or a predisposition to a condition associated with a loss of elastic fibers. Administration of a prophylactic agent can occur prior to the manifestation of symptoms characteristic of the decrease in LOXL1, such that a condition is prevented or, alternatively, delayed in its progression. Depending on the type of LOXL1 aberrance, for example, a LOXL1 enhancer can be used for treating the subject. The appropriate agent can be determined based on screening assays described herein.

As used herein, "treatment" means the application or administration of a LOXL1 enhancer therapeutic agent to a subject (e.g., a human or a veterinary or experimental animal subject), or application or administration of a therapeutic agent to an isolated tissue or cell line from a subject, who has a condition, a symptom of condition, or a predisposition to get a condition, with the purpose to cure, heal, alleviate, relieve, alter, remedy, ameliorate, improve, prevent, or affect the disease, symptoms of the condition, or the predisposition to get the condition. A LOXL1 enhancer therapeutic agent includes, but is not limited to, small molecules including peptidomimetics, peptoids, nucleic acids (e.g., nucleic acids encoding a LOXL1 polypeptide or active fragment thereof), aptamers, carbohydrates, polysaccharides, non-nucleic acid small organic molecules, inorganic molecules, polypeptides, antibodies, ribozymes, and drugs.

As used herein, an active fragment of a LOXL1 polypeptide retains the ability to oxidize lysine residues in elastin and collagen. For example, an active fragment can be missing a portion of the N-terminal sequence but retaining the C-terminal enzymatic domain (e.g., a fragment comprising from amino acids about 145, 179, 326, 338, to about 574, referring to the human sequence, GenBank Acc. No. AAH15090). An active fragments can include the C-terminal 28 kD of the polypeptide. Fragments can be generated by recombinant DNA techniques known in the art, or can be produced by enzymatic digestion of all or part of a full length LOXL1 polypeptide (i.e., amino acids 1-574 of the human sequence), e.g., digestion with bone morphogenetic protein-1 (BMP-1; see Borel et al., supra). Such fragments can comprise the N-terminal portion of the sequence that is conserved between LOX, LOXL1, LOXL2, LOXL3, and LOXL4, e.g., comprising the putative copper-binding site, the lysine tyrosylquinone cofactor formation, and/or the cytokine receptor-like domain (see, e.g., Maki, Dissertation: LYSYL OXIDASES, *Cloning and Characterization of the Fourth and the Fifth Human Lysyl Oxidase Isoenzymes, and the Consequences of a Targeted Inactivation of the First Described Lysyl Oxidase Isoenzyme in Mice*, Collagen Research Unit, Biocenter Oulu and Department of Medical Biochemistry and Molecular Biology, University of Oulu (2002)). Smaller or larger fragments can also be used.

Some LOXL1-related conditions can be caused, at least in part, by a detrimentally low level of a LOXL1 polypeptide, or by the presence of a LOXL1 polypeptide exhibiting detrimental activity. As such, an increase in the level and/or activity of such polypeptides would bring about the amelioration of symptoms associated with the condition. Successful treatment of such LOXL1-related conditions can be brought about by techniques that serve to increase the expression or activity of LOXL1 polypeptides.

LOXL1-related conditions, or conditions associated with a reduction in LOXL1 polypeptide expression, include conditions associated with a loss of elastic fibers. For example, such conditions include clinical syndromes resembling generalized elastolysis affecting skin, lung, large arteries and other organs. These conditions include: the loss of skin elasticity (i.e., wrinkly and loose skin), chronic obstructive pulmonary disease (COPD; e.g., emphysema, asthma, and chronic bronchitis), pelvic organ prolapse and urinary incontinence (common in elderly and multiparous women), vascular diseases (including aortic dissection, aneurisms, systolic high blood pressure, and stroke), and degradation of the elastic lamina of the Bruch's membrane in the eye, which contributes to choroidal neovascularization in age-related macular degeneration.

LOXL1 in the Skin

Human skin is composed of multiple strata, including the epidermis and the dermis. The mechanical properties of the skin, such as elasticity, are controlled by the density and geometry of the structural network of collagen and elastic fiber tissue. Damaged collagen and elastin lose their contractile properties, resulting in skin wrinkling and skin surface roughness. (Pasquali-Ronchetti and Baccarani-Contri, *Microsc. Res Tech.* 38(4), 428-35 (1997)). With normal and accelerated aging, skin can acquire sags, stretch marks, bumps, bruises or wrinkles, and the texture of the skin roughens. In the context of conditions associated with the loss of skin elasticity (i.e., wrinkly and loose skin), the goal of treatment is to increase skin elasticity. Such an increase can be measured using a number of methods. For example, an increase in skin elasticity can be measured by the naked eye, e.g., an increase in an aesthetic quality of the skin, an increase in tightness or decrease in wrinkling. Other empirical methods of measuring an improvement in skin elasticity are also available, e.g., using a ballistometer (Cyberderm, Media, Pa.), Cutometer® (Courage & Khazaka Electronic GmbH, Cologne, Germany), Comeometer®, (Courage & Khazaka Electronic GmbH, Cologne, Germany), Skin-Visiometer®, (Courage & Khazaka Electronic GmbH, Cologne, Germany) or Reviscometer® (Courage & Khazaka Electronic GmbH, Cologne, Germany). For example, see, e.g., U.S. Pat. No. 5,804,594. Since loss of elasticity associated with the normal aging process is believed to be due at least in part to loss of LOXL1 activity, an individual who wishes to delay or reverse signs of aging associated with a diminution in LOXL1 expression and/or activity can benefit from the methods of treatment or prevention described herein. In addition, those who are susceptible to premature or otherwise abnormal aging, or who for other reasons have or are likely to have loose or wrinkly skin (e.g., due to weight loss or pregnancy) can also benefit from the methods described herein to increase skin elasticity, and to improve the aesthetic appearance of skin, e.g., preventing, ameliorating, treating and/or reducing lines and/or wrinkles.

Pulmonary Disease

In certain pulmonary diseases such as emphysema, the fiber network within the lung is progressively destroyed. As a result, recoil pressures within the lung decrease and areas of the lung become hyperinflated, negatively impacting lung function. In the context of chronic obstructive pulmonary disease (COPD; e.g., emphysema, asthma and chronic bronchitis), the goal of treatment is to increase the elasticity of the airway. Individuals who have COPD, or who are at risk of having COPD (i.e., smokers or those who are otherwise susceptible to COPD), can benefit from the methods described herein. In some embodiments, the methods described herein are conducted before, concurrently with, or after lung volume reduction surgery (LVRS).

Pelvic Organ Prolapse/Urinary Incontinence

Approximately one in nine Caucasian women will have surgery for pelvic organ prolapse or urinary incontinence before the age of 80 (Olsen et al., *Obstet. Gynecol.* 89(4), 501-6 (1997)). Pelvic organ prolapse is believed to be associated in part with the loss of elastic fibers that form part of the structural support in the bladder, uterus, vagina and rectum. When this support is lost, the organs drop, placing pressure on the vagina or even descending through the vaginal opening. Urinary incontinence is a common result, and can also occur independently of pelvic organ prolapse. In the context of treatment of pelvic organ prolapse and/or urinary incontinence, the methods described herein can be used to induce recovery from prolapse and improve continence.

Urinary incontinence in the elderly is a gender-specific condition with different etiology between the sexes (Romanzi, *J. Gend. Specif. Med.* 4, 14-20 (2001)). Incontinence can be divided into several types. Stress urinary incontinence (SUI), the leakage of urine during increased abdominal pressure such as when laughing or coughing, is the most common forms of incontinence among elderly women (Resnick, *JAMA* 280, 2034-5 (1998); Diokno et al., *J. Urol.* 148, 1817-21 (1992)). SUI stems primarily not from bladder dysfunction, but rather from ineffective urethra closure (Cheater and Castleden, *Baillieres Best Pract. Res. Clin. Obstet. Gynaecol.* 14, 183-205 (2000); Ulmsten and Falconer, *Curr Opin Obstet. Gynecol.* 11, 509-515 (1999)). An effective closure of the urethra requires the concerted action of various anatomical structures connected to the organ. It is widely accepted that structural and functional integrity of the suburethral vaginal wall, the paraurethral connective tissues and the pubourethral ligaments are key factors in maintaining continence. Damage to pelvic tissues such as the suburethral vaginal wall and the paraurethral connective tissues are thought to be major underlying causes (Ulmsten and Falconer, supra (1999)).

The two epidemiologic factors most strongly associated with development of SUI are vaginal delivery of children (Turan et al., *Gynecol. Obstet. Invest.* 41, 132-4 (1996); Thomas et al., *Br. Med. J.* 281, 1243-5 (1980)) and advanced age (Thomas et al., supra (1980)). Vaginal delivery can injure the nerve, muscle, and connective tissues responsible for maintaining continence (Retzky and Rogers, *Clin. Symp.* 47, 2-32 (1995)). The muscles of the pelvic floor and the pubourethral ligaments, which support the urethra, can be overstretched and weakened during vaginal delivery, leading to incontinence (Sultan et al., *Br. J. Hosp. Med.* 55, 575-9 (1996)). In addition, the pudendal nerve, which supplies the skeletal muscle of the urethra, can be stretched and crushed during childbirth, leading to denervation of the external urethral sphincter (EUS) (Snooks et al., *Int. J. Colorectal. Dis.* 1, 20-4 (1986); Allen et al., *Br. J. Obstet. Gynaecol.* 97, 770-9 (1990)). Repeat damage via multiple childbirths, or multiparity, can further exacerbate incontinence, although the greatest damage appears to occur with the first vaginal delivery, causing a sharp increase in the prevalence of incontinence in primipara (Viktrup and Lose, *Int. Urogynecol. J. Pelvic. Floor. Dysfunct.* 11, 336-40 (2000)). Incontinence often does not become clinically evident until menopause, years after the initial childbirth injury, suggesting that biochemical and physiological changes with age contribute to the development of SUI (Retzky and Rogers, supra (1995); Makinen et al., *Maturitas* 22, 233-8 (1995)). Pelvic organ prolapse (POP) is another debilitating condition common in elderly women that is also linked to pelvic floor injury incurred in multiple childbirths. POP can both cause and/or exacerbate urinary incontinence.

Research into the histopathology of urinary incontinence has historically focused on changes in the collagen fibers in the involved tissues (Rechberger et al., *Eur J. Obstet. Gynecol. Reprod. Biol.* 49, 187-91 (1993); Cheater and Castelden, supra (2000)). In fact, one form of treatment for this condition is the use of injectable collagens. In addition to collagen, pelvic organs and adjoining connecting tissues are also rich in elastic fibers. Elastic fibers confer elasticity and resilience to tissues that are normally subjected to stretching and expansile forces (Mecham and Davis, in Yurchenco et al., eds., *Extracellular Matrix Assembly and Structure*, 281-314 (Academic Press, New York, 1994)).

Elastic fibers are laid down during discrete developmental periods and remain stable. An exception is the uterine tract where they undergo cycles of deposition and resorption. The uterine tract undergoes enormous expansion during pregnancy and rapid resorptive involution post partum. In addition, the uterine cervix expand and becomes softer in preparation for parturition, through a physiological process known as cervical ripening which degrades collagen and elastic fibers and softens the uterine wall (Leppert, *Clin. Obstet. Gynecol.* 38, 267-79 (1995); Bryant-Greenwood and Schwabe, *Endocr. Rev.* 15, 5-26 (1994)). Thus by necessity, connective tissues in the uterine tract undergo active remodeling; both elastic and collagen fibers are degraded and re-synthesized through the reproductive cycle (Woessner and Brewer, *Biochem. J.* 89, 75-82 (1963); Starcher and Percival, *Connect. Tissue. Res.* 13, 207-15 (1985)). Hence any defect in connective tissue remodeling in the uterine tract will likely exacerbate tissue damages suffered through pregnancy/parturition.

Vascular Diseases

The elastic properties of the large blood vessels are due to the presence of elastic fibers in the extracellular space. The primary load-bearing components of the aortic wall are collagen fibrils, smooth muscle cells, and elastic fibers. The collagen fibrils bear loads in the circumferential direction, whereas elastic fibers provide longitudinal as well as circumferential support. It is believed that changes in the interface between collagen fibrils, elastic fibers, and smooth muscle during aging and in connective tissue disorders leads to changes in the viscoelasticity of the vessel wall (Silver et al., *Crit. Rev. Biomed. Eng.* 29(3), 279-301 (2001)). Thus, in the context of the treatment of vascular diseases associated with the loss of elasticity, including aortic dissection, aneurisms, systolic high blood pressure, and stroke, the methods described herein can be used to reduce vascular stiffening and improve vascular tone.

Modulating LOXL1

In some embodiments, to modulate LOXL1 expression or activity (e.g., for therapeutic purposes), a cell is contacted with a LOXL1 nucleic acid or polypeptide (or active fragment thereof), or an agent that modulates one or more of the activities of LOXL1 polypeptide activity associated with the cell. An agent that modulates LOXL1 polypeptide activity can be, e.g., an agent as described herein, such as a nucleic acid or a polypeptide, a naturally-occurring binding partner of a LOXL1 polypeptide (e.g., a LOXL1 substrate such as tropoelastin), a LOXL1 antibody, a LOXL1 agonist, a peptidomimetic of a LOXL1 agonist, or other small molecule. The agent can be synthetic, or naturally-occurring. The cell can be an isolated cell, e.g., a cell removed from a subject or a cultured cell, or can be a cell in situ in a subject.

A LOXL1 enhancer agent can, in some embodiments, stimulate one or more LOXL1 activities. Examples of such stimulatory agents include active LOXL1 polypeptide or an active fragment thereof, and a nucleic acid molecule encoding a LOXL1 polypeptide or active fragment thereof. In another embodiment, the agent inhibits one or more LOXL1 activities. Examples of such inhibitory agents include antisense LOXL1 nucleic acid molecules or siRNAs, anti-LOXL1 antibodies, and LOXL1 inhibitors. These modulatory methods can be performed in vitro (e.g., by culturing a cell with the agent) or, alternatively, in vivo (e.g., by administering the agent to a subject). Thus, an individual afflicted with a condition characterized by aberrant (i.e., decreased) expression or activity of a LOXL1 polypeptide or nucleic acid molecule can be treated using a LOXL1 agent. The method of treatment can involve administering an agent (e.g., an agent identified by a screening assay described herein), or combination of agents that modulates (e.g., up regulates) LOXL1 expression or activity. Thus, in some embodiments, the method involves administering a LOXL1 polypeptide or nucleic acid molecule as therapy to compensate for reduced LOXL1 expression or activity.

Stimulation of LOXL1 activity or expression is desirable in situations in which LOXL1 is detrimentally downregulated and/or in which increased LOXL1 activity is likely to have a beneficial effect. Likewise, inhibition of LOXL1 activity is desirable in situations in which LOXL1 is detrimentally upregulated and/or in which decreased LOXL1 activity is likely to have a beneficial effect.

As defined herein, a therapeutically effective amount of a LOXL1 nucleic acid or polypeptide composition is a dosage effective to treat or prevent a particular condition for which it is administered. The dose will depend on the composition selected, i.e., a polypeptide or nucleic acid. The compositions can be administered from one or more times per day to one or more times per week; including once every other day. The skilled artisan will appreciate that certain factors may influence the dosage and timing required to effectively treat a subject, including but not limited to the severity of the condition, previous treatments, the general health and/or age of the subject, and other conditions present. Moreover, treatment of a subject with a therapeutically effective amount of the therapeutic LOXL1 compositions of the invention can include a single treatment or a series of treatments, as well as multiple (i.e., recurring) series of treatments.

Dosage, toxicity and therapeutic efficacy of such LOXL1 compositions can be determined by pharmaceutical procedures known in the art in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$ Compositions that exhibit high therapeutic indices are preferred. While compositions that exhibit toxic side effects may be used, care should be taken to design a delivery system that targets such compositions locally to the site of affected tissue to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The invention further includes pharmaceutical compositions comprising a LOXL1 enhancer, for use in the treatment of conditions associated with loss of in elastic fibers. Such compositions typically include a LOXL1 enhancer, and a pharmaceutically acceptable carrier. As used herein, a LOXL1 enhancer can be a LOXL1 nucleic acid or polypeptide (or active fragment thereof) or other positive modulator of LOXL1 activity or expression, e.g., a compound that increases LOXL1 activity or expression, e.g., identified by a method described herein. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A LOXL1 enhancer pharmaceutical composition is formulated to be compatible with its intended route of administration. Examples of routes of administration include parenteral (e.g., intravenous, intradermal, or subcutaneous), oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

LOXL1 enhancer pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active LOXL1 enhancer in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation are vacuum drying and freeze-drying which yields a powder of the active ingredient plus any additional desired ingredient from a previously sterile-filtered solution thereof.

Oral LOXL1 enhancer compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the LOXL1 enhancer can be delivered in the form of an aerosol spray from pressured container or dispenser which contains a suitable propellant, e.g., a gas such as carbon dioxide, or a nebulizer. Such methods include those described in U.S. Pat. No. 6,468,798. Administration by inhalation may be particularly suitable for methods of treating conditions associated with the loss of elastic fibers affecting the lungs, e.g., chronic obstructive pulmonary disease (COPD), e.g., emphysema, asthma, or chronic bronchitis.

Systemic administration of a LOXL1 enhancer can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Transdermal administration of a LOXL1 enhancer can be used, e.g., for the treatment or prevention of a skin condition associated with the loss of in elastic fibers in the skin, i.e., loose and/or wrinkly skin associated with aging, pregnancy, or weight loss.

In some embodiments, compositions comprising a LOXL1 enhancer for transdermal application can further comprise cosmetically-acceptable carriers or vehicles and any optional components. A number of such cosmetically acceptable carriers, vehicles and optional components are known in the art and include carriers and vehicles suitable for application to skin (e.g., sunscreens, creams, milks, lotions, masks, serums, etc.), see, e.g., U.S. Pat. Nos. 6,645,512 and 6,641,824. In particular, optional components that may be desirable include, but are not limited to absorbents, anti-acne actives, anti-caking agents, anti-cellulite agents, anti-foaming agents, anti-fungal actives, anti-inflammatory actives, anti-microbial actives, anti-oxidants, antiperspirant/deodorant actives, anti-skin atrophy actives, anti-viral agents, anti-wrinkle actives, artificial tanning agents and accelerators, astringents, barrier repair agents, binders, buffering agents, bulking agents, chelating agents, colorants, dyes, enzymes, essential oils, film formers, flavors, fragrances, humectants, hydrocolloids, light diffusers, nail enamels, opacifying agents, optical brighteners, optical modifiers, particulates, perfumes, pH adjusters, sequestering agents, skin conditioners/moisturizers, skin feel modifiers, skin protectants, skin sensates, skin treating agents, skin exfoliating agents, skin lightening agents, skin soothing and/or healing agents, skin thickeners, sunscreen actives, topical anesthetics, vitamin compounds, and combinations thereof.

The LOXL1 enhancer compositions can also be prepared in the form of suppositories (e.g., with conventional suppository bases such as cocoa butter and other glycerides) or retention enemas for rectal or vaginal delivery. Such suppositories can be used particularly for the treatment of conditions associated with the loss of in elastic fibers that affect the pelvic organs, e.g., pelvic organ prolapse and/or urinary incontinence, inter alia.

LOXL1 enhancer compositions comprising nucleic acids can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., *Clin. Immunol. Immunopathol.* 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, LOXL1 enhancer compositions are prepared with carriers that will protect against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using techniques known in the art. The materials can also be obtained commercially, e.g., from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration for the treatment or prevention of a condition associated with the loss of elastic fibers.

Screening Methods

The invention further provides methods (also referred to herein as "screening assays") for identifying modulators, i.e., candidate or test compounds or agents (e.g., polypeptides, peptides, peptidomimetics, peptoids, small molecules or other drugs) that specifically bind to LOXL1 polypeptides or nucleic acids, and/or modulate, e.g., have a enhancing or inhibitory effect on, for example, LOXL1 expression or LOXL1 activity. Compounds thus identified can be used to modulate the activity of LOXL1 polypeptides in a therapeutic protocol, to elaborate the biological function of the LOXL1 polypeptide, or to identify compounds that disrupt normal LOXL1 gene interactions. Compounds that positively modulate (i.e., increase) the activity or expression of LOXL1 polypeptides are LOXL1 enhancers. In some embodiments, test compounds are compounds whose ability to modulate LOXL1 activity or expression is unknown. In some embodiments, candidate compounds are compounds with a demonstrated ability to modulate LOXL1 activity or expression.

In one embodiment, the invention provides assays for screening candidate or test compounds that are substrates of a LOXL1 polypeptide or a biologically active fragment thereof. In another embodiment, the invention provides assays for screening candidate or test compounds that bind to or modulate the activity of a LOXL1 polypeptide or a biologically active fragment thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., *J. Med. Chem.* 37, 2678-2685 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Des.* 12, 145 (1997)).

Examples of methods for the synthesis of molecular libraries can be found in the art, for example in: DeWitt et al., *Proc. Natl. Acad. Sci. U.S.A.* 90, 6909 (1993); Erb et al., *Proc. Natl. Acad. Sci. U.S.A.* 91, 11422 (1994); Zuckermann et al., *J. Med. Chem.* 37, 2678 (1994); Cho et al., *Science* 261, 1303 (1993); Carrell et al., *Angew. Chem. Int. Ed. Engl.* 33, 2059 (1994); Carell et al., *Angew. Chem. Int. Ed. Engl.* 33, 2061 (1994); and in Gallop et al., *J. Med. Chem.* 37, 1233 (1994).

Libraries of compounds can be presented in solution (e.g., Houghten, *Biotechniques* 13, 412-421 (1992)), or on beads (Lam, *Nature* 354, 82-84 (1991)), chips (Fodor, *Nature* 364, 555-556 (1993)), bacteria (Ladner, U.S. Pat. No. 5,223,409), spores (Ladner, U.S. Pat. No. 5,223,409), plasmids (Cull et al., *Proc Natl. Acad Sci U.S.A.* 89, 1865-1869 (1992)), or on phage (Scott and Smith, *Science* 249, 386-390 (1990); Devlin, *Science* 249, 404-406 (1990); Cwirla et al., *Proc. Natl. Acad. Sci. U.S.A.* 87, 6378-6382 (1990); Felici, *J. Mol. Biol.* 222, 301-310 (1991); Ladner, supra).

In one embodiment, an assay is a cell-based assay in which a cell that expresses a LOXL1 polypeptide or biologically active fragment thereof is contacted with a test compound, and the ability of the test compound to modulate a LOXL1 activity is determined. Determining the ability of the test compound to modulate a LOXL1 activity can be accomplished by monitoring, for example, elastic fiber formation or levels of elastin, tropoelastin, and/or desmosine. In some embodiments, the assay comprises determining desmosine levels in the extracellular matrix of cultured cells. The cell, for example, can be of mammalian origin, e.g., human. In some embodiments, an assay is one in which LOXL1 lysyl oxidase activity is assayed directly in vitro, e.g., using synthetic peptide substrates, e.g., 1,5-diaminopentane (see Palamakumbura et al., *Analyt. Biochem.* 300, 245-251 (2002), describing a fluorescent assay) or all or part of tropoelastin (monomer of elastin) (see Borel et al., *J. Biol. Chem.* 276, 48944-48949 (2001)). A number of assays of LOXL1 activity are known in the art, see, e.g., Palamakumbura et al., supra (2002), Borel et al., supra (2001); and references cited in Kagan and Li, supra (2003).

The ability of the test compound to (i) modulate LOXL1 binding to a second compound, e.g., a LOXL1 substrate such as elastin, or to (ii) bind to LOXL1 directly can also be evaluated. This can be accomplished, for example, by coupling the compound, e.g., the substrate, with a radioisotope or enzymatic label such that binding of the compound, e.g., the substrate, to LOXL1 can be determined by detecting the labeled compound, e.g., substrate, in a complex. Alternatively, LOXL1 can be coupled with a radioisotope or enzymatic label to monitor the ability of a test compound to modulate LOXL1 binding to a LOXL1 substrate in a complex. For example, compounds (e.g., LOXL1 substrates) can be labeled with $^{125}I$, $^{35}S$, $^{14}C$, or $^3H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a test compound to interact with LOXL1 can be evaluated with or without the labeling of any of the interactants. For example, a microphysiometer can be used to detect the interaction of a compound with LOXL1 without the labeling of either the compound or the LOXL1. McConnell et al., *Science* 257, 1906-1912 (1992). A "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and LOXL1.

In yet another embodiment, a cell-free assay is provided in which a LOXL1 polypeptide or biologically active fragment thereof is contacted with a test compound and the ability of the test compound to bind to the LOXL1 polypeptide or biologically active fragment thereof is evaluated. In some embodiments, biologically active fragments of the LOXL1 polypeptides to be used in assays of the present invention include fragments which participate in interactions with non-LOXL1 molecules, e.g., fragments with high surface probability scores.

Soluble and/or membrane-associated forms of isolated polypeptides (e.g., LOXL1 polypeptides or biologically active fragments thereof) can be used in the cell-free assays of the invention. When membrane-associated forms of the polypeptide are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays can involve preparing a reaction mixture of the LOXL1 polypeptide and the test compound, and allowing the reaction to proceed under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' polypeptide molecule may simply utilize the natural fluorescent energy of tryptophan residues. Labels are chosen that emit different wavelengths of light, such that the 'acceptor' molecule label may be differentiated from that of the 'donor.' Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through fluorometric detection means known in the art (e.g., using a fluorimeter).

In another embodiment, determining the ability of the LOXL1 polypeptide to bind to a target molecule can be accomplished using real-time Biomolecular Interaction Analysis (BIA) (see, e.g., Sjolander and Urbaniczky, *Anal. Chem.* 63, 2338-2345 (1991) and Szabo et al., *Curr. Opin. Struct. Biol.* 5, 699-705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, either a LOXL1 polypeptide or active fragment thereof, or a test compound, is anchored onto a solid phase. The LOXL1/test compound complexes anchored on the solid phase can be detected at the end of the reaction. Typically, the LOXL1 polypeptide can be anchored onto a solid surface, and the test compound, (which is not anchored), can be labeled, either directly or indirectly, with detectable labels known in the art and discussed herein.

It may be desirable to immobilize either LOXL1, an anti-LOXL1 antibody or its target molecule to facilitate separation of complexed from uncomplexed forms of one or both of the polypeptides, as well as to accommodate automation of the assay. Binding of a test compound to a LOXL1 polypeptide, or interaction of a LOXL1 polypeptide with a target molecule in the presence and absence of a test compound, can be accomplished in any vessel suitable for containing the reactants. Examples of such vessels include microtiter plates, test tubes, and micro-centrifuge tubes. In one embodiment, a fusion polypeptide can be provided which adds a domain that allows one or both of the polypeptides to be bound to a matrix. For example, glutathione-S-transferase/LOXL1 fusion polypeptides or glutathione-S-transferase/peptide test compound fusion polypeptides can be adsorbed onto glutathione Sepharose™ beads (Sigma Chemical, St. Louis, Mo.) or glutathione derivatized microtiter plates, which are then combined with either the test compound or the test compound and either the non-adsorbed target polypeptide or LOXL1 polypeptide, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of LOXL1 binding or activity determined using techniques known in the art.

Other techniques for immobilizing either a LOXL1 polypeptide or a test compound on matrices include using conjugation of biotin and streptavidin. Biotinylated LOXL1 polypeptide or test compounds can be prepared from biotin-NHS(N-hydroxy-succinimide) using techniques known in the art (e.g., biotinylation kit, Pierce Chemicals, Rockford, Ill.), and immobilized, for example, in the wells of streptavidin-coated multi-well (e.g., 96-well) plates (Pierce Chemical).

To conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies specific for LOXL1 polypeptide or test compounds that do not interfere with binding of the LOXL1 polypeptide to its target molecule. Such antibodies can be derivatized to the wells of the plate, and unbound target or LOXL1 polypeptide trapped in the wells by antibody conjugation. Methods for detecting such complexes, in addition to those described above for the GST-immobilized complexes, include immunodetection of complexes using antibodies reactive with the LOXL1 polypeptide or target molecule, as well as enzyme-linked assays which rely on detecting an enzymatic activity associated with the LOXL1 polypeptide or target molecule.

Alternatively, cell free assays can be conducted in a liquid phase. In such an assay, the reaction products are separated from unreacted components, by any of a number of techniques known in the art, including but not limited to: differential centrifugation (see, for example, Rivas and Minton, *Trends Biochem. Sci.* 18, 284-287 (1993)); chromatography (gel filtration chromatography, ion-exchange chromatography); electrophoresis (see, e.g., Ausubel et al., eds., *Current Protocols in Molecular Biology* 1999, J. Wiley: New York.); and immunoprecipitation (see, for example, Ausubel et al., eds. (1999) supra). Such resins and chromatographic techniques are known to one skilled in the art (see, e.g., Heegaard, *J. Mol. Recognit.* 11, 141-148 (1998); Hage and Tweed, *J. Chromatogr. B. Biomed. Sci. Appl.* 699:499-525 (1997)). Further, fluorescence energy transfer may also be conveniently utilized, as described herein, to detect binding without further purification of the complex from solution.

In some embodiments, the assay includes contacting a LOXL1 polypeptide or biologically active fragment thereof with a known compound that binds LOXL1 (e.g., fibulin-5 or tropoelastin) to form an assay mixture, contacting the assay mixture with a test compound, and determining the ability of the test compound to interact with a LOXL1 polypeptide, wherein determining the ability of the test compound to interact with a LOXL1 polypeptide includes determining the ability of the test compound to preferentially bind to LOXL1 or biologically active fragment thereof, as compared to the known compound.

The LOXL1 polypeptides described herein can, in vivo, interact with one or more cellular or extracellular macromolecules, such as polypeptides, e.g., tropoelastin or fibulin-5. For the purposes of this discussion, such cellular and extracellular macromolecules are referred to herein as "binding partners." Compounds that disrupt or enhance such interactions can be useful in regulating the activity of the LOXL1 polypeptide. Such compounds can include, but are not limited to, molecules such as antibodies, peptides, and small molecules. In an alternative embodiment, the invention provides methods for determining the ability of the test compound to modulate the activity of a LOXL1 polypeptide on a LOXL1 binding partner.

To identify compounds that modulate (e.g., disrupt or enhance) an interaction between the LOXL1 polypeptide and its cellular or extracellular binding partner(s) (e.g., tropoelastin or fibulin-5), a reaction mixture containing the LOXL1 polypeptide and the binding partner is prepared, under conditions and for a time sufficient to allow the two products to form complex. To test a potential modulatory agent, the reaction mixture is provided in the presence and absence of the test compound. The test compound can be initially included in the reaction mixture, or can be added at a time subsequent to the addition of the LOXL1 gene and its cellular or extracellular binding partner. As a reference, control reaction mixtures can be incubated without the test compound or with a placebo. The formation of any complexes between the LOXL1 polypeptide and the cellular or extracellular binding partner, or the formation of elastin polymers, e.g., elastin dimers, is then detected. The formation of a complex in the control reaction, but not in the reaction mixture containing the test compound, indicates that the compound disrupts with the interaction of the LOXL1 polypeptide and the interactive binding partner. The formation of more complexes in the test reaction, or faster formation of complexes in the test reactions, as compared to the reference reaction, indicates that the test compound enhances the interaction of the LOXL1 polypeptide and the binding partner. Additionally, complex formation within reaction mixtures containing the test compound and normal LOXL1 polypeptide can also be compared to complex formation within reaction mixtures containing the test compound and a mutant LOXL1 polypeptide, or another lysyl oxidase, e.g., LOX, LOXL2, LOXL3 or LOXL4. This comparison can be important in those cases wherein it is desirable to identify compounds that modulate interactions of mutant but not normal LOXL1 polypeptides, or to identify compounds that specifically affect LOXL1.

In yet another aspect, a LOXL1 polypeptide can be used as a "bait protein" in a two-hybrid assay or three-hybrid assay (see, e.g., U.S. Pat. No. 5,283,317; Zervos et al., *Cell* 72, 223-232 (1993); Madura et al., *J. Biol. Chem.* 268, 12046-12054 (1993); Bartel et al., *Biotechniques* 14, 920-924 (1993); Iwabuchi et al., *Oncogene* 8, 1693-1696 (1993); and International Patent Application No. WO 94/10300), to identify other polypeptides that bind to or interact with LOXL1 ("LOXL1-binding polypeptides" or "LOXL1-bp") and are involved in LOXL1 activity. Such LOXL1-bps can be activators or inhibitors of an activity of a LOXL1 polypeptide.

The two-hybrid system is based on the modular nature of most transcription factors, which consist of separable DNA-binding and activation domains. Briefly, the assay utilizes two different DNA constructs. In one construct, the gene that codes for a LOXL1 polypeptide is fused to a gene encoding the DNA binding domain of a known transcription factor (e.g., GAL-4). In the other construct, a DNA sequence, e.g., from a library of DNA sequences, that encodes an unidentified polypeptide ("prey" or "sample") is fused to a gene that codes for the activation domain of the known transcription factor. (Alternatively, the LOXL1 polypeptide can be fused to the activator domain.) If the "bait" and the "prey" polypeptides are able to interact, in vivo, forming a LOXL1-dependent complex, the DNA-binding and activation domains of the transcription factor are brought into close proximity. This proximity allows transcription of a reporter gene (e.g., lacZ) that is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with the LOXL1 polypeptide.

In another embodiment, modulators of LOXL1 expression, e.g., transcriptional activators or translational enhancers, can be identified and used in the method described herein. For example, a cell or cell free mixture is contacted with a test or candidate compound and the expression of LOXL1 mRNA or polypeptide is evaluated, relative to the level of expression of LOXL1 mRNA or polypeptide in the absence of the test or candidate compound. When expression of LOXL1 mRNA or polypeptide is greater (i.e., statistically significantly greater) in the presence of the test or candidate compound than in its absence, the test or candidate compound is identified as a stimulator of LOXL1 mRNA or polypeptide expression. Alternatively, when expression of LOXL1 mRNA or polypeptide is less (i.e., statistically significantly less) in the presence of the test or candidate compound than in its absence, the test or candidate compound is identified as an inhibitor of LOXL1 mRNA or polypeptide expression. The level of LOXL1 mRNA or polypeptide expression can be determined by methods described herein for detecting LOXL1 mRNA or polypeptide.

In another aspect, the invention pertains to a combination of two or more of the assays described herein. For example, a modulating agent can be identified using a cell-based or a cell free assay, and the ability of the agent to modulate the activity of a LOXL1 polypeptide can be confirmed in vivo, e.g., in an animal such as an animal model for a disease associated with the loss of elastic fibers, as described herein.

This invention further pertains to novel agents identified by the above-described screening assays. Accordingly, it is within the scope of this invention to further use an agent identified as described herein (e.g., a LOXL1 modulating agent, an antisense LOXL1 nucleic acid molecule, a LOXL1-specific antibody, or a LOXL1-binding partner) in an appropriate animal model to determine the efficacy, toxicity, side effects, or mechanism of action, of treatment with such an agent. Furthermore, novel agents identified by the above-described screening assays can be used for treatments as described herein.

Monitoring the influence of agents (e.g., drugs) on the expression or activity of a LOXL1 polypeptide can be applied in clinical trials. For example, the effectiveness of an agent determined by a screening assay as described herein to increase LOXL1 gene expression, polypeptide levels, or upregulate LOXL1 activity, can be monitored in clinical trials of subjects exhibiting decreased LOXL1 gene expression, polypeptide levels, or downregulated LOXL1 activity. Alternatively, the effectiveness of an agent determined by a screening assay to decrease LOXL1 gene expression, polypeptide levels, or downregulate LOXL1 activity, can be monitored in clinical trials of subjects exhibiting increased LOXL1 gene expression, polypeptide levels, or upregulated LOXL1 activity. In such clinical trials, the expression or activity of a LOXL1 gene, and preferably, other genes that have been implicated in, for example, a LOXL1-associated disorder can be used as a "read out" or markers of the phenotype of a particular cell.

The invention is further described in the following examples, which do not limit the scope of the invention described in the claims.

EXAMPLES

Example 1

LOXL1 Expression in Normal Mice

To investigate the expression pattern of LOXL1 in normal mice, immunolocalization experiments were performed.

Two polyclonal anti-LOXL1 antibodies and one anti-LOX antibody were generated by immunizing rabbits with His-tagged recombinant polypeptides (based on GenBank accession nos. AAK97375 and AAH18439). One antibody, α-LOXL1N (spanning amino acid residues 175-313 of murine LOXL1) is unique to LOXL1, but it does not recognize the cleavage product (36 kDa; FIG. 1C). Three LOXL1 variant polypeptides are seen in FIG. 1C: a 64 kDa matching the predicted full-length form absent the secretory signal peptide, a 67 kDa band presumed to be the full-length form with the signal peptide, and a 36 kDa band matching the cleavage product retaining the C-terminal conserved domain (Borel et al., *J. Biol. Chem.* 276, 48944-48949 (2001)). The latter interpretation is supported by the observation that this band was not detected by the LOXL1N antibody. Immunoblotting shows no compensatory increase of the prototypic LOX in the Loxl1$^{-/-}$ mutant. Two LOX variants (24 kDa and 32 kDa) are detected in adult aorta.

The α-LOXL1C (spanning residues 313-607) and α-LOX (spanning residues 204-411 of murine LOX) antibodies encompassed the C-terminal region conserved among LOX family members. To obtain antibodies that were monospecific, affinity-purified α-LOXL1C and α-LOX antibodies were put through columns containing the respective homologous polypeptides immobilized on agarose beads (Amino-Link Plus, Pierce).

Fibulin-5 antibody (BSYN1923), made in rabbits, was described previously (Yanagisawa et al., Nature 415, 168-171 (2002)). The following elastin and fibrillins-1 and 2 antibodies were obtained from Elastin Products Company (Owensville, Mo.): PR385 (rabbit anti-mouse elastin, exons 6-17); PR387 (rabbit anti-mouse elastin, exons 31-36); RT675 (goat anti-rat elastin) used for double-labeling of elastin with LOXL1, LOX or fibulin-5; PR210AP (rabbit anti-fibrillin-1); PR225 (rabbit anti-fibrillin-2). EBP antibody (EBP2112) (Mochizuki et al., *J. Biol. Chem.* 277, 44854-44863 (2002)) was a gift from Dr. A. Hinek (The Hospital for Sick Children, Toronto, Canada).

To examine co-localization of LOXL1 and fibulin-5 in the extracellular matrix, a rat arterial smooth muscle cell line (PAC-1) known to deposit extracellular matrix material (Rothman et al., *Circulation* 86, 1977-1986 (1992)) was cultured and used for double-labeling immunofluorescence for LOXL1 and fibulin-5. Full length fibulin-5 and LOXL1 cDNAs (without the signal peptide sequences) were inserted into the pcDNA3 and the pEGFP-C2 vectors, respectively. Following transient transfection in COS-7 cells, recombinant polypeptides were visualized with the aid of the EGFP tag and by staining with the fibulin-5 antibody.

Secondary antibodies conjugated to Alexa 488 (green) and Alexa 594 (red) were from Molecular Probes (Eugene, Oreg.). To perform double labeling for LOXL1 and fibulin-5, LOXL1 antibody was tagged with biotin using the Mini-Biotin protein labeling kit (Molecular Probes) and detected by fluorochrome-conjugated streptavidin. For immunoblotting, total tissue homogenates probed with antibody PR385 were used to detect soluble elastin (monomer and dimer). Unless otherwise noted, the tissues was extracted first with PBS and then with 6M urea, and the urea extracts were used for immunoblotting analysis of LOXL1 and LOX.

In wild-type mice, LOXL1 was normally present in a stable fibrillar pattern that co-localized with elastic fibers. In the mutant mice, elastin staining appeared as fragments or aggregates, and was fully solubilized only under denaturing conditions (e.g., 6 M urea).

LOXL1 expression in the uterine tract declined as the animals aged. At 18 months, an age approaching the mouse equivalent of a "menopause," LOXL1 mRNA and protein were nearly extinguished. Tropoelastin accumulated and elastin fibers were lost concomitant with the decline of LOXL1 (see Example 8). Thus, elastic fiber maintenance in the uterine tract becomes "defective" in wild-type animals as they age.

Example 2

LOXL1 Knockout Mice

To investigate a possible role for LOXL1 in elastogenesis, its expression was ablated in mice by gene targeting (FIGS. 1A-B). Briefly, 6-kb and 3-kb genomic fragments flanking exon 1 of the Loxl1 gene (GenBank Accession is BC037999) were amplified by PCR from 129/Sv mouse DNA. These fragments were cloned into the pGT-N29 vector on either side of the neon gene. The targeting vector also contained a diphtheria toxin expression cassette (DTA) as a negative selection marker (FIG. 1A). The targeting vector was linearized and electroporated into R1 embryonic stem (ES) cells. Multiple targeted ES clones were identified by PCR (FIG. 1B), and targeted clones were microinjected into C57BL/6 blastocysts and crossed the chimeras with C57BL/6 mice. Mice heterozygous or homozygous for the targeted allele were identified by PCR (FIG. 1B). Primer sequences are shown in Table 1. Fibulin-5 homozygous mutant mice were previously described (Yanagisawa et al., Nature 415, 168-171 (2002)).

The LOXL1-deficient mice were viable. Females were initially fertile, producing viable offspring, but about 20% underwent pelvic prolapse about 2-3 days after giving birth to their first litter. Significant pelvic organ prolapse was seen in Loxl1$^{-/-}$ female mice at 2 days and 14 days post partum. Although the prolapse retracted at PP14, permanent pelvic descent remained as indicated by a large genitourinary bulge. No significant prolapse was seen in the WT mice; all loxl1$^{-/-}$ mice developed prolapse after delivery of their second or third litter. Prolapsed tissues retracted over time (generally a period of several weeks), but prominent pelvic descent remained, indicating permanent damage to the pelvic floor. Gross inspection of dissected pelvic tissues found a multitude of abnormalities. The circumference of the vaginal wall was several fold the normal size and had a very different texture compared to the WT. The urethra was no longer tightly attached to the suburethral vaginal wall, leading to hypermobility of the urethra. The uterus was dilated, appeared thinner (almost translucent) and lacked resilience. The uterine cervix was stretched to several fold the normal size, consistent with a loss of resiliency. The surrounding connective tissues also appeared loose and lacked tensile strength compared to the WT. By histological examination, the urethras of WT mice showed close apposition of the luminal walls, whereas those of the mutant show poor apposition as well as reduced elastic fiber content in the paraurethral connective tissues, as well as opened urethral lumen and generally loose organization of the connective tissues.

Both genders of Loxl1$^{-/-}$ mice developed enlarged airspaces of the lung, which was apparent in the mutant lung by gross inspection, particularly along the periphery; increased laxity and redundancy of the skin as compared to wild type; rectal prolapse; and intestinal diverticula.

TABLE 1

Primer sequences

| Primer | Sequence | SEQ ID NO: |
|---|---|---|
| S31 | 5'-GTGATAAGCAGGAGCCAGAGCAAG | 1 |
| S32 | 5'-ACACGTCGGTGCTGGGATCA | 2 |
| D5 | 5'-CCTTCGTAAACCAGTATGAGAACTACGATC | 3 |

TABLE 1-continued

Primer sequences

| Primer | Sequence | SEQ ID NO: |
|---|---|---|
| N5 | 5'-CGAGATCAGCAGCCTCTGTTCCAC | 4 |
| N3 | 5'-CCGGAGAACCTGCGTGCAATC | 5 |
| L5 | 5'-TTACACACACACTTGCAGGCCAG | 6 |

Example 3

Elastic Fiber Anatomy in the Uterine Tract of LOXL1 Knockout Mice, Pre- and Post-Partum To investigate the elastic fiber anatomy in the uterine tract of LOXL1 knockout mice, immunolocalization experiments were performed.

Mouse tissues were fixed in 4% formaldehyde, and embedded them in paraffin. Histochemical (Verhoeff and Hart's stain) staining and histologic examinations of multiple tissues were performed on the paraffin-embedded sections using standard methodology. For electron microscopy, the tissues were fixed in 2.5% glutaraldehyde, 1% formaldehyde in sodium cacodylate buffer, and embedded in Epon Immunoblotting and immunofluorescence staining of unfixed cryosections was performed as described (Hong et al., *J. Biol. Chem.* 276, 12091-12099 (2001)).

Elastic fibers in the uterine tract of the knockout mice were thick, up to 3 µm in diameter and prominent under Nomarski optics. Uterine elastic fibers appeared normal in nulliparous Loxl1$^{-/-}$ females. Pregnancy and birth, however, exposed the inability of the mutant to lay down normal elastic fibers during connective tissue remodeling. When examined at one week post partum, Loxl1$^{-/-}$ mice had fragmented elastin polymers as shown by immunostaining. Verhoeff and Hart's histochemical staining also indicated loss of elastic fibers. Electron microscopy showed collagen fibrils to be of comparable abundance and morphology. It is notable that in older postpartum uterine tissues the elastin polymerization defect was much more pronounced than in young (30 days) virgin uterine tissues, indicating a heightened requirement for LOXL1 in the re-deposition of elastin polymer through the reproductive cycle.

Example 4

Elastic Fiber Anatomy in the Lungs, Skin and Aorta of LOXL1 Knockout Mice

To investigate the elastic fiber anatomy in the lungs, skin, and aorta of LOXL1 knockout mice, immunolocalization experiments were performed as described herein.

Histologic and electron microscopic examinations were performed as described above. The trachea and lungs were removed together and fixed under 20 cm water pressure. Microscopic examination found enlarged alveoli in the mutant lung, indicating emphysematous changes consistent with an elastic fiber defect. Elastic fibers in the lower dermis of skin were also fragmented and reduced. Immunostaining for elastin in the elastic lamina of the aorta appeared diffuse and weak, suggesting reduced and imprecise elastin polymer deposition. This was supported by ultrastructural examinations showing disorganized elastin core and a reduction in amorphous elastin polymer. Immunobloting showed that tropoelastin accumulated in multiple adult tissues, often with a concomitant reduction in cross-linked intermediate (FIG. 2A, 72 kDa, elastin monomer (tropoelastin); 144 kDa, elastin dimer).

These data also suggest that new elastin polymer deposition continues in wild-type (WT) adult tissues, but is arrested by the loss of LOXL1. A selective role for LOXL1 in elastin, but not collagen, metabolism is supported by measurements of desmosine and hydroxyproline (FIGS. 2B-C), which represent elastin and collagen crosslinks, respectively. Desmosine and hydroxyproline analysis was performed as described previously (Starcher et al., *Connect. Tissue Res.* 31, 133-140 (1995)). Desmosine levels were significantly reduced in multiple Loxl1$^{-/-}$ tissues, whereas hydroxyproline levels remained unchanged. Specifically, Desmosine was reduced by 40-53% in the postpartum uterus (PPU), lung and skin, but not in the virgin uterus (VU) of the mutant (FIG. 2B). No significant differences were found in the hydroxyproline contents between the wild-type and mutant tissues (FIG. 2C). n=5-10 animals.

Example 5

Immunolocalization of LOXL1 in Wild-Type Mice

LOXL1 is closely related to the prototypic LOX, and both are widely expressed. Although no difference in substrate selectivity was detected in vitro, the inability of LOX to compensate for LOXL1 and the largely non-overlapping phenotypes of the gene-ablated mutants (Maki et al., *Circulation* 106, 2503-2509 (2002); Hornstra et al., *J. Biol. Chem.* 278, 14387-14393 (2003)) suggest functional differences in vivo. By immunolocalization using monospecific antibodies, LOXL1 appeared closely associated with the elastic lamina whereas LOX was broadly distributed. In the skin (lower dermis) and the uterus (myometrium), LOXL1 fully overlaps with elastic fibers, whereas LOX was diffusely distributed.

These data indicate that LOXL1, but not LOX, is specifically targeted to sites of elastogenesis. Thus LOXL1 appears to function primarily to guide elastin deposition in a spatially defined manner, a prerequisite for the formation of functional elastic fibers. The localization pattern of LOX, on the other hand, appears consistent with a role in crosslinking both collagens and elastin (Maki et al., *Circulation* 106, 2503-2509 (2002); Hornstra et al., *J. Biol. Chem.* 278, 14387-14393 (2003)).

Example 6

LOXL1 Interacts with Fibulin-5

To determine the molecular interactions that could account for the targeting of LOXL1 to the scaffold of elastogenesis, protein interaction screens were performed using the yeast two hybrid system. The Matchmaker™ Two-Hybrid System 3 (Clontech) was used for yeast two-hybrid screens as previously described (Hong et al., *J. Biol. Chem.* 276, 12091-12099 (2001)). An adult rat lung library in the pACT2 vector was from Clontech. The initial library screen utilized the full-length LOXL1 as the bait. To determine the interacting domains, a series of deletion constructs was prepared (FIG. 3A; horizontal lines underneath the protein schematic diagrams) and tested by co-transformation in yeast. For the GST pull-downs and co-immunoprecipitation experiments, the L3 and F3 coding sequences (FIG. 3A) were inserted into pET- 28a and pGEX-4T1 vectors, respectively, and purified soluble fractions were used for the GST pull-down assay. Glutathione Sepharose™ 4 Fast Flow beads were used to pull down GST and GST-L3, and the inputs and eluates were probed with anti-T7 Tag HRP conjugate (Novagen) and chicken anti-GST antibodies on immunoblots. For co-immunoprecipitation, wild-type mouse lungs were extracted with 4 M urea, dialysed the supernatant overnight at 4° C. against PBS, and performed immunoprecipitation with a-LOXL1C antibody and protein G-agarose.

Figure 3B:
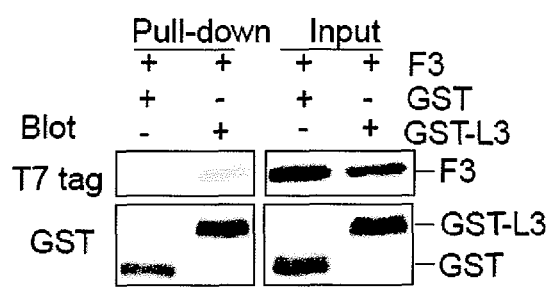
FIG. 3B is a set of blots showing the results of GST pull-down assay, illustrating an in vitro direct interaction between fibulin-5 and LOXL1. Input: 16% of eluate.
Figure 3C:
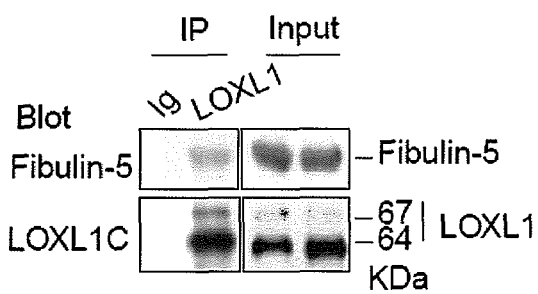
FIG. 3C is a set of blots showing the results of co-immunoprecipitation of fibulin-5 with LOXL1 in lung extracts suggesting interaction in vivo. Input: 50% of eluate.
Figure 3D:
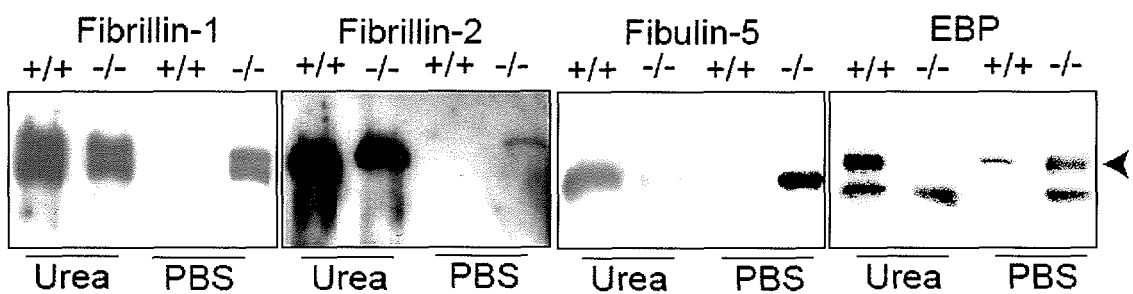
FIG. 3D is a set of four immunoblots showing the results of analyses of elastic fiber-associated polypeptides from wild-type (+/+) and Loxl1$^{-/-}$ uterine tissues. PBS, tissue extracts with PBS. Urea, tissue extracts with 6 M urea after PBS extraction.

With LOXL1 as a bait, fibulin-5 was found to be a potential interacting partner. Further analyses showed that a region immediately N-terminal to the catalytic domain (L3) of LOXL1 interacted with the C-terminal portion (F3) of fibulin-5 (FIG. 3A). Their physical interaction in vitro was confirmed using pull-down assays (FIG. 3B). Co-immunoprecipitation of fibulin-5 with LOXL1 from tissue extracts (FIG. 3C) suggested an in vivo interaction. In cell culture, LOXL1 and fibulin-5 were shown to colocalize in a perinuclear compartment in transiently transfected COS-7 cells and to colocalize in extracellular deposits produced by vascular smooth muscle cells. In extracellular matrix deposited by a cultured vascular smooth muscle cell line (PAC-1), the two polypeptides are found together in fibrillar and dot patterns. In tissue sections, LOXL1 and fibulin-5 colocalized in a fibrillar pattern that also fully overlapped with elastin immunostaining. Interestingly, loss of fibulin-5 abolished the fibrillar staining pattern of LOXL1, but not vice versa. These observations suggest that fibulin-5 localizes to sites of elastogenesis independent of LOXL1 and that fibulin-5 might be responsible for tethering LOXL1 to these sites. LOXL1, on the other hand, appears to stabilize the fibrillar form of fibulin-5 as indicated by the increased solubility of fibulin-5 in absence of LOXL1 (FIG. 3D). As shown in FIG. 3D, Fibulin-5 and EBP in the mutant were mostly shifted to the soluble fraction (PBS extractable) from an insoluble fraction (urea extractable). In the right most panel, a 67-kDa band (arrow head) represents EBP. The identity of a smaller (59-kDa) polypeptide is uncertain, but it was previously found in uterus and may be a smaller EBP isoform (Yamamoto et al., *Cell Biol. Int.* 26, 441-449 (2002)).

The increased solubility of fibulin-5 may be due to disruption of elastin polymer in the LOXL1 mutant tissues. Loss of LOXL1 also increased the soluble fraction of EBP, a protein known to associate with elastic fibers. Fibrillins 1 and 2, components of microfibrils, were only partially affected by the loss of LOXL1 (FIG. 3D) consistent with the fact that not all microfibrils are associated with elastic fibers.

The above data demonstrate the in vivo relevance of LOXL1/fibulin-5 interaction. Further support comes from the similarity between the two mutant mouse models, both of which exhibit specific defects in elastogenesis. In general, elastic fiber defects in the fibulin-5 mutant mice manifests earlier than in the LOXL1 mutant. For example, one-day-old fibulin-5 mutant mice show tortuosity of the aorta; this is not seen in age-matched LOXL1 mutant. Young (thirty day old) LOXL1 mutant mice have abundant elastic fibers in their uterine tract and skin, as revealed by elastin immunostaining. By the same assay, young fibulin-5 mutant mice have few elastic fibers in these tissues. While a role for LOXL1 in elastic fiber development could not be ruled out, these phenotypic differences are consistent with the notion that the elastic fiber defect seen in the LOXL1 mutant can be attributed, at least in part, to a defect in elastic fiber renewal in adult tissues, rather than in development.

Example 7

Urinary Incontinence in Female Loxl1$^{-/-}$ Mice

The urethra is normally tightly adhered to the suburethral vaginal wall. The paraurethral connective tissue and the suburethral vaginal wall in humans are key determinants in the ability of the urethra to maintain secure closure (Cheater and Castleden, supra (2000); Ulmsten and Flaconer, supra (1999); Keane and O'Sullivan, *Baillieres Best Pract. Res. Clin. Obstet. Gynaecol.* 14, 207-26 (2000)). Human urinary incontinence has a gender-specific etiology and, among women, childbearing is a major risk factor (Romanzi, *J. Gend. Specif. Med.* 4, 14-20 (2001)). A history of prolapse and pelvic tissue damage might also impact urethral function in mice. Indeed, multiparous loxl1$^{-/-}$ females appeared unable to maintain urine storage. There was no voiding of the bladder upon euthanasia, as would invariably occur in all WT mice and in loxl1$^{-/-}$ male mice. Dissection of pelvic organs of the loxl1$^{-/-}$ females found the urinary bladders relaxed and empty in most cases, thus ruling out urinary retention as the cause for lack of voiding. Absence of urine could also be caused by kidney failure, which would shut down urine production. Tests for the filtration function (blood urea nitrogen) and histological examinations of the kidney were carried out. Both were found to be normal, thus ruling out an overt kidney disease. These results indicate that parous loxl1$^{-/-}$ female mice developed ineffective urethral closure and urinary incontinence. This interpretation is consistent with the overt damage to the pelvic floor and paraurethral connective tissues.

To further investigate this hypothesis, a direct assay for urinary incontinence was carried out in these mice, in comparison with age-matched, parous WT mice. This was done by recording urination patterns and outputs in a custom-built micturition chamber over an extended period of time. A mouse micturation chamber, designed to measure urinary output in real time, was custom built by Columbus Instruments (Columbus, Ohio). This chamber was adapted from the mouse metabolic cage offered by Columbus Instruments. The micturation chamber had a wire mesh bottom, which was connected to a funnel. The inside surface of the funnel was coated with molten paraffin and re-coated after several uses to minimize trapping of liquid in the funnel. Directly below the funnel was a collection tube sitting on top of a scale and connected to a computer. Changes in the weight of the collection tube were monitored and recorded continuously in real time. Initial tests had confirmed that urine drops as small as 50 µl in volume could be reliably collected and recorded by the system. To begin the study, mice were placed on residue-free diet (Lactaid brand whole milk) for 24 hours prior to being placed inside the chamber. This was done to prevent feces droppings from interfering with measurement of urine output. Mice had continued free access to the milk and were tested in this chamber one at a time. Data were analyzed and plotted using the Multi-Device Interface software provided by Columbus Instruments.

Data analyses included univariate statistics to calculate group means and standard deviations, and plots of frequency distributions. Consideration was given to transforming data (to logarithms) if distributions appear skewed. Mean group differences were evaluated by t-test and ANOVA for normally distributed data and by nonparametric statistics (the Mann-Whitney U test) for non-normal distributions or small samples. Relationships between measurements were assessed by the Pearson product moment correlation for parametric data and by the Spearman rank correlation for ordinal data or for skewed distributions that include statistical outliers. Multiple linear regression techniques were applied to relationships between continuous variables that need to be adjusted for significant covariates. Statistical analyses was performed using JMP, version 3.2 (SAS Institute, Cary, N.C.), SAS, version 6.12 (SAS Institute, Cary, N.C.).

Figure 6A:
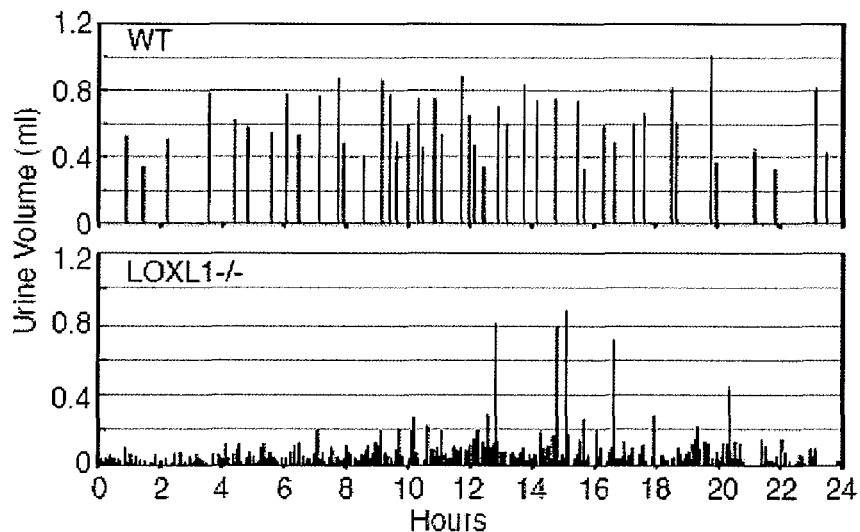
FIG. 6A is a pair of exemplary urinary profiles, for a wild type mouse (top graph) and a mutant mouse (bottom graph), showing urinary volume over 24 hours. Urine measurement were made using a metabolic cage. The urinary behavior of Loxl1$^{-/-}$ parous females (n=8) was recorded, with WT parous females as control (n=7).
Figure 6B:
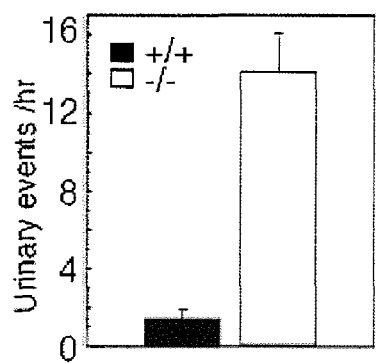
FIGS. 6B and 6C are bar graphs illustrating the results of statistical analysis of data, including the data in FIG. 6A, for urinary events/hr (6B) and urinary volume (ml/event, 6C).
Figure 6C:
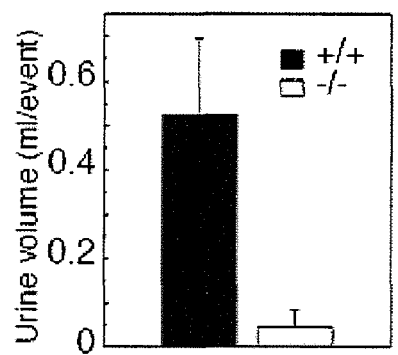

As shown in FIGS. 6A-C, on average the mutant LOXL1 knockout mice had a 10-fold higher frequency of urinary events over a 24-hour period (WT: 1.450±0.430 events/hr (n=7), vs. KO: 14.1444±1.895 events/hr (n=8); p<0.001)). Consistent with a much higher urination frequency, urinary output per event in the mutant mice was only one tenth that of the WT mice. (WT: 0.528±0.167 ml/event (n=7), vs. KO: 0.049±0.034 ml/event (n=8); p<0.001); total volume: WT: 18.374±5.811 ml/24 hours, KO: 16.633±11.542 ml/24 hours). These differences are statistically highly significant. These differences cannot be explained by a major difference in the metabolic states of these animals. The total urinary output and total amount of fluid drank over a 24-hour period were not significantly different between the mutant and WT mice. These data show that the loxl1 mutant mice produced urine normally but suffered from urinary incontinence.

Figure 7:
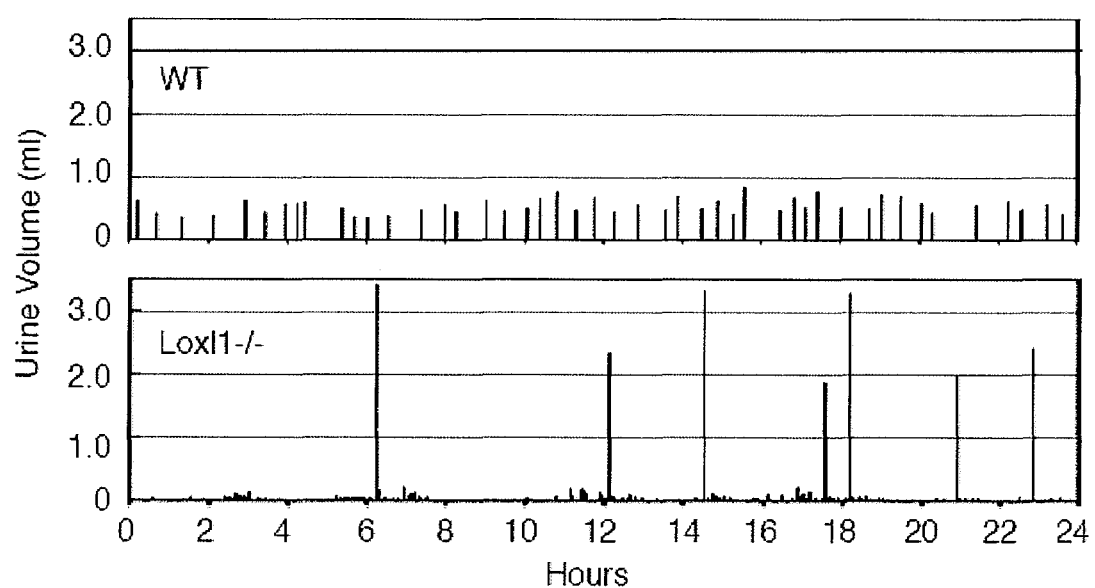
FIG. 7 is a pair of exemplary urinary profile graphs of a wild type mouse (top graph) and a mutant mouse with urinary retention (bottom graph), showing urinary volume over 24 hours.

Paradoxically, in a small percentage of mice severe urinary retention was also seen as evidenced by enormously distended bladders filled with urine (FIG. 7, top panel), and confirmed by rare and exceedingly high-volume urinary events (FIG. 7, bottom panel). After 24 hours, the mutant with urinary retention gave 7±2 major events and the mean urine volume for major events was 2.661±0.431 ml/big event (n=3, p<0.05). In contrast, average output/event in the WT mice was 0.5 ml. Thus, when urinary retention occurred, output per urinary event typically reached over 3 ml, a value that we had never seen in WT animals. Although an opposite manifestation to incontinence, the etiology is in fact likely to be the same. This is because pelvic prolapse and connective tissue damage can lead to hypermobility of the urethra. When the latter becomes twisted or otherwise developed hard kinks along its lengths, urine flow through the urethra could be partly or completely blocked off Urine flow could only take place after the bladder and urethral pressures reach a very high level or when positions of the pelvic organs shift as a result of movement. Urinary retention could further damage the bladder sphincter and exacerbate incontinence once the urethra reopens. Such clinical complications are well documented in human patients (Romanzi et al., *J. Urol.* 161, 581-6 (1999)). These findings highlight common aspects in the pathophysiology of urinary incontinence between this mouse model and human patients.

These findings have implications for understanding the common form of human urinary incontinence, affecting well over 30% of women over the age of sixty (Romanzi, *J. Gend. Specif. Med.* 4, 14-20 (2001)). Although the condition was already aptly described some ninety years ago as "an affection beginning in the middle life, most common in multiparae" (Kelly & Dumm, *Surg. Gynec. Obst.* 18, 444-450 (1914)), a pathogenic mechanism at the molecular level remains elusive. Research and treatment have traditionally focused on collagen metabolism. This data indicates that elastic fiber homeostasis, which critically depends on LOXL1, is key to maintaining the structural and functional integrity of the lower urinary tract. Thus, therapeutic interventions aimed at promoting endogenous LOXL1 or providing exogenous replacement LOXL1 are an effective approach to solving this problem.

Example 8

Changes in LOXL1 Expression Through the Reproductive Cycles and During Aging

The uterine tract undergoes enormous expansion during pregnancy and rapid resorptive involution post partum. Being a key component for tissue remodeling through this period, LOXL1 expression in WT animals might be expected to fluctuate in response to changing physiological needs.

Total RNA was isolated using the TRIzol reagent (GIBCO). First strand cDNA synthesis was primed with oligo $(dT)_{20}$ using the ThermoScript™ RT-PCR System (Invitrogen). PCR primers for amplifying LOXL1 were P1 (5'-CGCGTTACGAGGACTACGGAG; SEQ ID NO:7) and P2 (5'-GACCATTCTGGTTGGGTCGGT; SEQ ID NO:8). PCR primers for elastin were P3 (5'-CTGGATCGCTGGCTG-CATCCA; SEQ ID NO:9) and P4 (5'-GTCCAAAGCCAG-GTCTTGCTG; SEQ ID NO:10). Glyceraldehyde-3-phosphate dehydrogenase (GAPDH) was amplified together with LOXL1 and elastin targets in the same tube as an internal standard for quantification. PCR primers for GAPDH were P5 (5'TGAAGGTCGGTGTGAACGGATTTGGC; SEQ ID NO:11) and P6 (5'-CATGTAGGCCATGAGGTCCACCAC; SEQ ID NO:12). Pilot experiments were done to determine the optimal primer concentrations in these mixed PCR reactions. Finally, P1, P2, P3 and P4 primers were used at 0.15 μM. P5 and P6 primers were used at 0.1 μM. PCR products were separated on 1.5% agarose gels and the images were captured by Fluor-S™ MultiImager. Quantification was carried out using the Multi-Analyst software (Bio-Rad Laboratories).

Figure 4A:
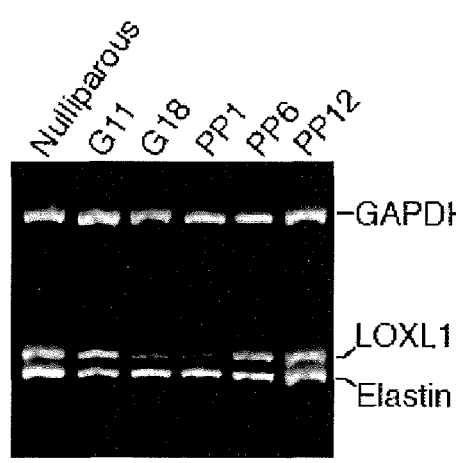
FIGS. 4A and 4B are a gel (4A) and line graph (4B) illustrating the results of analysis of LOXL1 mRNA through the reproductive cycle by RT-PCR.
Figure 4B:
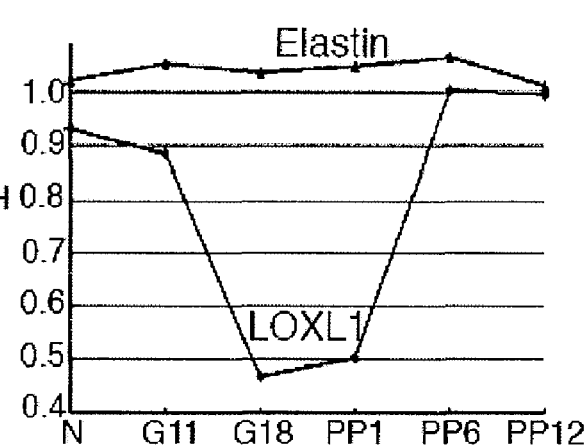

Indeed, LOXL1 mRNA in the uterine cervix fell to 20% of baseline perinatally and returned to baseline 6 days post partum (FIGS. 4A-B). Fluorescent photomicrography showing LOXL1 protein levels through the reproductive cycle, detected by immunoblotting, in a nulliparous mouse and in a parous mouse at 1 day (middle panel) and 12 days post partum. Immunofluorescence for LOXL1 shows absence of LOXL1 fibers at 1 day post partum in the uterine cervix. Red, LOXL1; blue, nuclear stain. LOXL1 protein also became undetectable in the uterine cervix at day one post partum. The temporal pattern of LOXL1 expression in the uterine cervix coincides with a physiological process in late pregnancy known as cervical ripening, regulated by hormones (Bryant-Greenwood and Schwabe, *Endocr. Rev.* 15, 5-26 (1994)). In preparation for parturition, cervical ripening leads to the breakdown of collagen and elastic fibers and softening of the uterine wall (Leppert, *Clin. Obstet. Gynecol.* 38, 267-79 (1995); Bryant-Greenwood and Schwabe, supra (1994)). Suppression of LOXL1 expression perinatally is consistent with the physiological needs of this period.

Figure 5A:
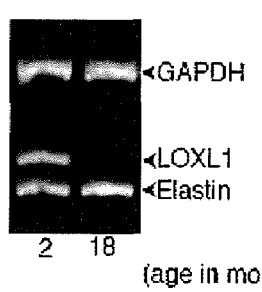
FIGS. 5A and 5B are a gel (5A) and bar graph (5B) illustrating the age-dependent decline of LOXL1 expression in the uterine tract, as detected by RT-PCR. WT mice at 2 months (young) and 18 months (old) of age were examined. On the left is a representative agarose gel analysis of PCR products, and on the right is a bar graph representing the percentage changes in LOXL1 expression. Values are the averages of three independent samples. GAPDH levels were used as internal normalization standards.
Figure 5B:
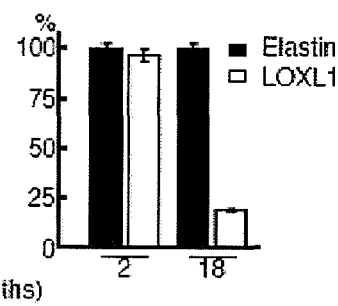
Figure 5C:
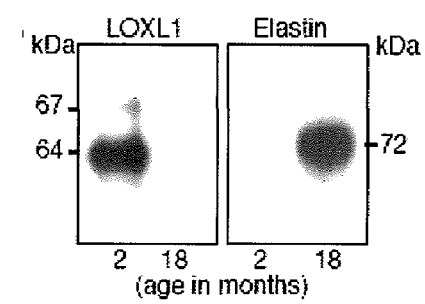
FIG. 5C is a pair of Western blots showing the results of a comparison of LOXL1 protein levels in the uteri of young and old mice by immunoblotting (left panel). LOXL1 is undetectable in the older animals. Loss of LOXL1 expression is correlated with an accumulation of tropoelastin in the older animals (right panel).

LOXL1 expression declined as the animals age, along with cessation of reproductive activity. At 18 months, an age approaching the mouse equivalent of a "menopause," LOXL1 mRNA (FIGS. 5A-B) and protein (FIG. 5C) were greatly diminished. In contrast, elastin (FIGS. 5A-B) mRNA remained little changed. As would be expected from our study of the LOXL1-deficient mice, tropoelastin accumulated and elastin fibers were reduced concomitant with the decline of LOXL1 expression (FIG. 5C). The observations that LOXL1 expression is highly regulated through the reproductive cycle and is extinguished in old age suggest that LOXL1 expression in the uterine tract may be under hormonal regulation.

Example 9

The Role of LOXL1 in Elastic Fiber Homeostasis in the Vascular System

Since elasticity is important in the normal physiology of the vasculature, a number of experiments were performed to evaluate that role of LOXL1 in the vascular system. Immunoelectron microscopy was used, and the results show that LOXL1 is highly expressed in the elastic lamina of large arteries of mice and rats of all ages, from weanlings to 6 months of age. In contrast, LOX, LOXL2, LOXL3 and LOXL4 did not demonstrate specific expression along the elastic, laminas of arteries. This observation provides further evidence that LXOL1, unique among the LOX family of proteins, is dedicated to elastogenesis in the vascular system.

Direct measurements of blood pressure in mice using a standard tail cuff method (Krege et al., *Hypertension* 25(5), 1111-1115 (1995)) demonstrated that the systolic pression in mice lacking LOXL1 is higher. WT mice: 119±8 mmHg, n=12. LOXL1 KO mice: 128±6 mmHg, n=10. This difference is statistically significant (p=0.025).

Using more invasive methods in which the sensor is placed directly inside the carotid artery (described in Hafezi-Moghadam et al., *Am. J. Physiol. Cell. Physiol.* 286, C876-C892. Epub 2003 Dec. 10. (2004)), hypertension was further confirmed.

Hypertension in the mutant mice is consistent with a more rigid and less elastic vascular wall. These data lend further support to our hypothesis that LOXL1 insufficiency, due either to allelic difference or advanced age, plays a role in the pathogenesis of hypertension in humans.

Example 10

Theoretical Model of LOXL1 in Elastogenesis

Figure 3E:
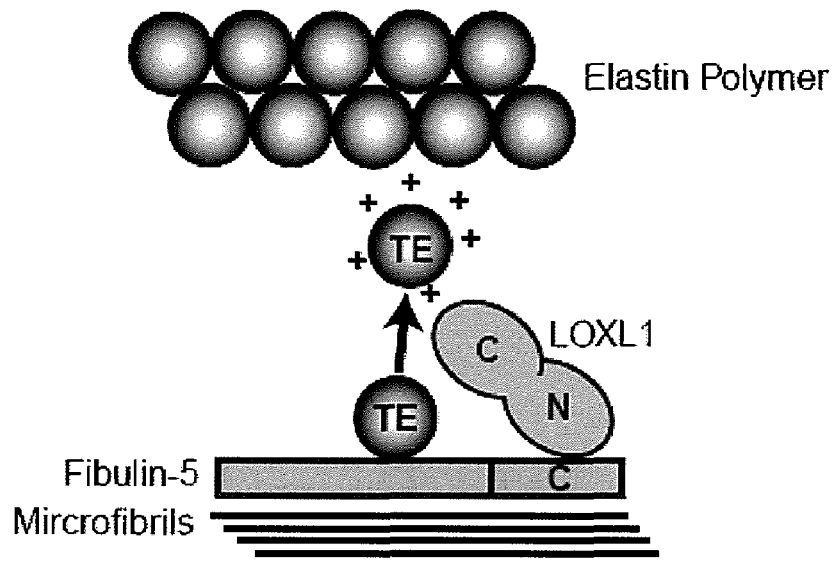
FIG. 3E is a diagrammatic illustration of a simplified model for the role of LOXL1 in elastogenesis. Possible tissue-specific variations and partial functional redundancies are not considered. The nature of the interaction between fibulin-5 and microfibrils remains unclear. TE, tropoelastin. The N-terminal unique region of LOXL1 binds to fibulin-5. C, C-terminal domains.

FIG. 3E is one model of how LOXL1 functions during elastic fiber renewal. Not wishing to be bound by theory, in this model, binding of fibulin-5 to both tropoelastin (Yanagisawa et al., *Nature* 415, 168-171 (2002)) and LOXL1 brings enzyme and substrate into juxtaposition for efficient and spatially restricted polymer formation. LOXL1 converts tropoelastin into a lysyl-deaminated form, and the "activated" tropoelastin associates with one another or deposits onto the existing polymer through coacervation (Vrhovski et al., *Eur. J. Biochem.* 258, 1-18 (1998)), followed by spontaneous covalent crosslinking. This allows the addition of elastin polymer at the interface next to the scaffold. LOXL1 binding to Fibulin-5 may also fulfill a regulatory role, given that cleavage of the N-terminal portion of LOXL1 activates its activity in vitro (Borel et al., *J. Biol. Chem.* 276, 48944-48949 (2001)), yet LOXL1 is present predominantly in the full length form in vivo.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having or at risk for loss of skin elasticity, the method comprising locally administering to the subject a therapeutically effective amount of a Lysyl Oxidase-Like-1 (LOXL1) polypeptide that is at least 95% identical to amino acids 26-574 of SEQ ID NO:13 and can catalyze crosslinking of tropoelastin to form elastin.

2. The method of claim 1, wherein the loss of skin elasticity is associated with wrinkly or loose skin.

3. The method of claim 1, wherein the loss of skin elasticity is associated with aging, weight loss, or pregnancy.

4. The method of claim 1, wherein the LOXL1 polypeptide comprises SEQ ID NO:13.

5. The method of claim 1, wherein the polypeptide comprises amino acids 26-574 of SEQ ID NO:13.

6. The method of claim 1, wherein the subject is a human, and the LOXL1 polypeptide comprises amino acids 26-574 of SEQ ID NO:13.

7. A method of treating the development or progression of loss of skin elasticity, the method comprising locally administering to a subject a therapeutically effective amount of a Lysyl Oxidase-Like-1 (LOXL1) polypeptide that is at least 95% identical to amino acids 26-574 SEQ ID NO: 13 and can catalyze crosslinking of tropoelastin to form elastin.

8. The method of claim 7, wherein the loss of skin elasticity is associated with wrinkly or loose skin.

9. The method of claim 7, wherein the loss of skin elasticity is associated with aging, weight loss, or pregnancy.

10. The method of claim 7, wherein the LOXL1 polypeptide comprises SEQ ID NO:13.

11. The method of claim 7, wherein the polypeptide comprises amino acids 26-574 of SEQ ID NO:13.

12. The method of claim 7, wherein the treatment results in an increase in elastin levels in the elastic lamina of the eye of the subject.

13. The method of claim 7, wherein the subject is a human, and the LOXL1 polypeptide comprises SEQ ID NO:13.

14. A method of treating a subject having or at risk for loss of skin elasticity, the method comprising locally administering to the subject a therapeutically effective amount of a Lysyl Oxidase-Like-1 (LOXL1) polypeptide that is at least 95% identical to amino acids 26-607 of SEQ ID NO:14 and can catalyze crosslinking of tropoelastin to form elastin.

15. The method of claim 14, wherein the polypeptide comprises amino acids 26-607 of SEQ ID NO:14.

16. The method of claim 14, wherein the polypeptide comprises SEQ ID NO:14.

17. A method of treating a subject having or at risk for loss of skin elasticity, the method comprising locally administering to the subject a therapeutically effective amount of a Lysyl Oxidase-Like-1 (LOXL1) polypeptide that is at least 95% identical to SEQ ID NO:15 and can catalyze crosslinking of tropoelastin to form elastin.

18. The method of claim 17, wherein the polypeptide comprises SEQ ID NO:15.

19. A method of treating a subject having or at risk for loss of skin elasticity, the method comprising locally administering to the subject a therapeutically effective amount of a Lysyl Oxidase-Like-1 (LOXL1) polypeptide that is at least 95% identical to SEQ ID NO: 16 and can catalyze crosslinking of tropoelastin to form elastin.

20. The method of claim 19, wherein the polypeptide comprises SEQ ID NO:16.

21. A method of treating the development or progression of loss of skin elasticity, the method comprising locally administering to a subject a therapeutically effective amount of a Lysyl Oxidase-Like-1 (LOXL1) polypeptide that is at least 95% identical to amino acids 26-607 of SEQ ID NO:14 and can catalyze crosslinking of tropoelastin to form elastin.

22. The method of claim 21, wherein the polypeptide comprises amino acids 26-607 of SEQ ID NO:14.

23. The method of claim 21, wherein the polypeptide comprises SEQ ID NO:14.

24. A method of treating the development or progression of loss of skin elasticity, the method comprising locally administering to a subject a therapeutically effective amount of a Lysyl Oxidase-Like-1 (LOXL1) polypeptide that is at least 95% identical to SEQ ID NO:15 and can catalyze crosslinking of tropoelastin to form elastin.

25. The method of claim 24, wherein the polypeptide comprises SEQ ID NO:15.

26. A method of treating the development or progression of loss of skin elasticity, the method comprising locally administering to a subject a therapeutically effective amount of a Lysyl Oxidase-Like-1 (LOXL1) polypeptide that is at least 95% identical to SEQ ID NO:16 and can catalyze crosslinking of tropoelastin to form elastin.

27. The method of claim 26, wherein the polypeptide comprises SEQ ID NO:16.

28. The method of claim 1, wherein the local administration is transdermal or topical administration.

29. The method of claim 7, wherein the local administration is transdermal or topical administration.

30. The method of claim 14, wherein the local administration is transdermal or topical administration.

31. The method of claim 17, wherein the local administration is transdermal or topical administration.

32. The method of claim 19, wherein the local administration is transdermal or topical administration.

33. The method of claim 21, wherein the local administration is transdermal or topical administration.

34. The method of claim 24, wherein the local administration is transdermal or topical administration.

35. The method of claim 26, wherein the local administration is transdermal or topical administration.

36. The method of claim 1, wherein the LOXL1 polypeptide is administered in an ointment, salve, gel, or cream.

37. The method of claim 7, wherein the LOXL1 polypeptide is administered in an ointment, salve, gel, or cream.

38. The method of claim 14, wherein the LOXL1 polypeptide is administered in an ointment, salve, gel, or cream.

39. The method of claim 17, wherein the LOXL1 polypeptide is administered in an ointment, salve, gel, or cream.

40. The method of claim 19, wherein the LOXL1 polypeptide is administered in an ointment, salve, gel, or cream.

41. The method of claim 21, wherein the LOXL1 polypeptide is administered in an ointment, salve, gel, or cream.

42. The method of claim 24, wherein the LOXL1 polypeptide is administered in an ointment, salve, gel, or cream.

43. The method of claim 26, wherien the LOXL1 polypeptide is administered in an ointment, salve, gel, or cream.

* * * * *

UNITED STATES PATENT AND TRADEMARK OFFICE
CERTIFICATE OF CORRECTION

PATENT NO.         : 8,173,121 B2
APPLICATION NO.    : 12/699701
DATED              : May 8, 2012
INVENTOR(S)        : Tiansen Li and Xiaoqing Liu It is certified that error appears in the above-identified patent and that said Letters Patent is hereby corrected as shown below:

On Cover Page, Column 2 (Other Publications), line 2, delete "Aquisita," and insert -- Acquisita, --

On Cover Page, Column 2 (Other Publications), line 14, delete "elastogeneis," and insert -- elastogenesis, --

On Cover Page, Column 2 (Other Publications), line 48, delete "fibronogenesis," and insert -- fibrinogenesis, --

In Column 48, line 44, Claim 43, delete "wherien" and insert -- wherein --

Signed and Sealed this
Twenty-first Day of August, 2012

David J. Kappos
*Director of the United States Patent and Trademark Office*

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gtgataagca ggagccagag caag                                          24

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
acacgtcggt gctgggatca                                               20

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ccttcgtaaa ccagtatgag aactacgatc                                    30

<210> SEQ ID NO 4
<211> LENGTH: 24
<212> TYPE: DNA
<213> ORGANISM: Artificial Sequence
<220> FEATURE:
<223> OTHER INFORMATION: Primer
```

<400> SEQUENCE: 4
cgagatcagc agcctctgtt ccac                                              24

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ccggagaacc tgcgtgcaat c                                                 21

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ttacacacac acttgcaggc cag                                               23

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
cgcgttacga ggactacgga g                                                 21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gaccattctg gttgggtcgg t                                                 21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
ctggatcgct ggctgcatcc a                                                 21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gtccaaagcc aggtcttgct g                                                 21

<210> SEQ ID NO 11
<211> LENGTH: 26

```
<212> TYPE: DNA
<213> ORGANISM: Artificial Sequence
<220> FEATURE:
<223> OTHER INFORMATION: Primer

<400> SEQUENCE: 11
tgaaggtcgg tgtgaacgga tttggc                                          26

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
catgtaggcc atgaggtcca ccac                                            24

<210> SEQ ID NO 13
<211> LENGTH: 574
<212> TYPE: PRT
<213> ORGANISM: Homo sapiens

<400> SEQUENCE: 13

Met Ala Leu Ala Arg Gly Ser Arg Gln Leu Gly Ala Leu Val Trp Gly
 1               5                  10                  15

Ala Cys Leu Cys Val Leu Val His Gly Gln Ala Gln Pro Gly Gln
            20                  25                  30

Gly Ser Asp Pro Ala Arg Trp Arg Gln Leu Ile Gln Trp Glu Asn Asn
        35                  40                  45

Gly Gln Val Tyr Ser Leu Leu Asn Ser Gly Ser Glu Tyr Val Pro Ala
    50                  55                  60

Gly Pro Gln Arg Ser Glu Ser Ser Arg Val Leu Leu Ala Gly Ala
65                  70                  75                  80

Pro Gln Ala Gln Gln Arg Arg Ser His Gly Ser Pro Arg Arg Gln
                85                  90                  95

Ala Pro Ser Leu Pro Leu Pro Gly Arg Val Gly Ser Asp Thr Val Arg
            100                 105                 110

Gly Gln Ala Arg His Pro Phe Gly Phe Gly Gln Val Pro Asp Asn Trp
        115                 120                 125

Arg Glu Val Ala Val Gly Asp Ser Thr Gly Met Ala Arg Ala Arg Thr
    130                 135                 140

Ser Val Ser Gln Gln Arg His Gly Gly Ser Ala Ser Ser Val Ser Ala
145                 150                 155                 160

Ser Ala Phe Ala Ser Thr Tyr Arg Gln Gln Pro Ser Tyr Pro Gln Gln
                165                 170                 175

Phe Pro Tyr Pro Gln Ala Pro Phe Val Ser Gln Tyr Glu Asn Tyr Asp
            180                 185                 190

Pro Ala Ser Arg Thr Tyr Asp Gln Gly Phe Val Tyr Arg Pro Ala
        195                 200                 205

Gly Gly Gly Val Gly Ala Gly Ala Ala Val Ala Ser Ala Gly Val
    210                 215                 220

Ile Tyr Pro Tyr Gln Pro Arg Ala Arg Tyr Glu Glu Tyr Gly Gly Gly
225                 230                 235                 240

Glu Glu Leu Pro Glu Tyr Pro Gln Gly Phe Tyr Pro Ala Pro Glu
                245                 250                 255

Arg Pro Tyr Val Pro Pro Pro Pro Pro Asp Gly Leu Asp Arg
            260                 265                 270
```

```
Arg Tyr Ser His Ser Leu Tyr Ser Glu Gly Thr Pro Gly Phe Glu Gln
        275                 280                 285

Ala Tyr Pro Asp Pro Gly Pro Glu Ala Ala Gln Ala His Gly Gly Asp
        290                 295                 300

Pro Arg Leu Gly Trp Tyr Pro Tyr Ala Asn Pro Pro Glu Ala
305                 310                 315                 320

Tyr Gly Pro Pro Arg Ala Leu Glu Pro Pro Tyr Leu Pro Val Arg Ser
                    325                 330                 335

Ser Asp Thr Pro Pro Gly Gly Glu Arg Asn Gly Ala Gln Gln Gly
                340                 345                 350

Arg Leu Ser Val Gly Ser Val Tyr Arg Pro Asn Gln Asn Gly Arg Gly
                    355                 360                 365

Leu Pro Asp Leu Val Pro Asp Pro Asn Tyr Val Gln Ala Ser Thr Tyr
        370                 375                 380

Val Gln Arg Ala His Leu Tyr Ser Leu Arg Cys Ala Ala Glu Glu Lys
385                 390                 395                 400

Cys Leu Ala Ser Thr Ala Tyr Ala Pro Glu Ala Thr Asp Tyr Asp Val
                    405                 410                 415

Arg Val Leu Leu Arg Phe Pro Gln Arg Val Lys Asn Gln Gly Thr Ala
                    420                 425                 430

Asp Phe Leu Pro Asn Arg Pro Arg His Thr Trp Glu Trp His Ser Cys
        435                 440                 445

His Gln His Tyr His Ser Met Asp Glu Phe Ser His Tyr Asp Leu Leu
        450                 455                 460

Asp Ala Ala Thr Gly Lys Lys Val Ala Glu Gly His Lys Ala Ser Phe
465                 470                 475                 480

Cys Leu Glu Asp Ser Thr Cys Asp Phe Gly Asn Leu Lys Arg Tyr Ala
                    485                 490                 495

Cys Thr Ser His Thr Gln Gly Leu Ser Pro Gly Cys Tyr Asp Thr Tyr
                500                 505                 510

Asn Ala Asp Ile Asp Cys Gln Trp Ile Asp Ile Thr Asp Val Gln Pro
        515                 520                 525

Gly Asn Tyr Ile Leu Lys Val His Val Asn Pro Lys Tyr Ile Val Leu
        530                 535                 540

Glu Ser Asp Phe Thr Asn Asn Val Val Arg Cys Asn Ile His Tyr Thr
545                 550                 555                 560

Gly Arg Tyr Val Ser Ala Thr Asn Cys Lys Ile Val Gln Ser
                    565                 570

<210> SEQ ID NO 14
<211> LENGTH: 607
<212> TYPE: PRT
<213> ORGANISM: Mus musculus

<400> SEQUENCE: 14

Met Ala Leu Ala Gly Ala Gly Ser Gln Leu Arg Thr Leu Val Trp Ser
  1               5                  10                  15

Ala Cys Leu Cys Val Leu Val His Gly Gln Gln Ala Gln Pro Gly Gln
                 20                  25                  30

Gly Ser Asp Pro Gly Arg Trp Arg Gln Leu Ile Gln Trp Glu Asn Asn
            35                  40                  45

Gly Gln Val Tyr Ser Leu Leu Asn Ser Gly Ser Glu Tyr Val Pro Ala
        50                  55                  60

Gly Pro Gln Arg Gly Glu Thr Ser Ser Arg Val Leu Leu Ala Gly Ala
 65                 70                  75                  80
```

```
Pro Gln Thr Ser Gln Arg Arg Ser Gln Gly Gly Pro Arg Arg Gln
                85                  90                  95

Ala Pro Ser Leu Pro Leu Pro Gly Arg Val Gly Ser Asp Thr Val Arg
            100                 105                 110

Gly Gln Thr Arg His Pro Phe Gly Phe Gly Gln Val Pro Asp Asn Trp
            115                 120                 125

Arg Glu Val Ala Val Gly Asp Ser Thr Gly Met Ala Arg Ala Arg Thr
        130                 135                 140

Ser Val Ser Gln Gln Arg His Gly Gly Ser Ala Ser Ser Val Ser
145                 150                 155                 160

Ala Ser Ala Phe Ala Thr Thr Tyr Arg Gln Pro Ser Ser Tyr Pro Gln
                165                 170                 175

Gln Phe Pro Tyr Pro Gln Ala Pro Phe Val Asn Gln Tyr Glu Asn Tyr
            180                 185                 190

Asp Pro Ala Ser Arg Thr Tyr Glu Gln Gly Tyr Val Tyr Tyr Arg Gly
            195                 200                 205

Ala Gly Gly Met Gly Ala Gly Ala Ala Val Ala Ser Ala Gly
    210                 215                 220

Val Ile Tyr Pro Phe Gln Pro Arg Ala Arg Tyr Glu Asp Tyr Gly Gly
225                 230                 235                 240

Gly Gly Gly Glu Glu Gln Pro Glu Tyr Pro Ala Gln Gly Phe Tyr Pro
            245                 250                 255

Ala Pro Glu Arg Pro Tyr Val Pro Gln Pro Gln Pro Gln Pro
            260                 265                 270

Gln Pro Gln Pro Gln Pro Gln Pro Ser Asp Gly Leu Asp Arg Arg Tyr
            275                 280                 285

Ser His Ser Leu Tyr Asn Glu Gly Thr Pro Gly Phe Glu Gln Ala Tyr
            290                 295                 300

Pro Asp Pro Ser Thr Asp Val Ser Gln Ala Pro Ala Gly Ala Gly Gly
305                 310                 315                 320

Thr Tyr Gly Gly Ala Gly Asp Pro Arg Leu Gly Trp Tyr Pro Pro Tyr
            325                 330                 335

Ala Ala Asn Val Pro Pro Glu Ala Tyr Val Pro Pro Arg Ala Val Glu
            340                 345                 350

Pro Gln Pro Pro Phe Arg Val Leu Glu Pro Pro Tyr Leu Pro Val Arg
            355                 360                 365

Ser Ser Asp Ala Pro Ser Gln Gly Gly Glu Arg Asn Gly Ala Gln Gln
            370                 375                 380

Gly Arg Leu Ser Val Gly Ser Val Tyr Arg Pro Asn Gln Asn Gly Arg
385                 390                 395                 400

Gly Leu Pro Asp Leu Val Pro Asp Pro Asn Tyr Val Gln Ala Ser Thr
            405                 410                 415

Tyr Val Gln Arg Ala His Leu Tyr Ser Leu Arg Cys Ala Ala Glu Glu
            420                 425                 430

Lys Cys Leu Ala Ser Thr Ala Tyr Ala Pro Glu Ala Thr Asp Tyr Asp
            435                 440                 445

Leu Arg Val Leu Leu Arg Phe Pro Gln Arg Val Lys Asn Gln Gly Thr
            450                 455                 460

Ala Asp Phe Leu Pro Asn Arg Pro Arg His Thr Trp Glu Trp His Ser
465                 470                 475                 480

Cys His Gln His Tyr His Ser Met Asp Glu Phe Ser His Tyr Asp Leu
                485                 490                 495

Leu Asp Ala Ser Thr Gly Lys Lys Val Ala Glu Gly His Lys Ala Ser
            500                 505                 510
```

Phe Cys Leu Glu Asp Ser Thr Cys Asp Phe Gly Asn Leu Lys Arg Tyr
            515                 520                 525

Ala Cys Thr Ser His Thr Gln Gly Leu Ser Pro Gly Cys Tyr Asp Thr
        530                 535                 540

Tyr Asn Ala Asp Ile Asp Cys Gln Trp Ile Asp Ile Thr Asp Val Gln
545                 550                 555                 560

Pro Gly Asn Tyr Ile Leu Lys Val His Val Asn Pro Lys Tyr Ile Val
                565                 570                 575

Leu Glu Ser Asp Phe Thr Asn Asn Val Val Arg Cys Asn Ile His Tyr
            580                 585                 590

Thr Gly Arg Tyr Val Ser Thr Thr Asn Cys Lys Ile Val Gln Ser
        595                 600                 605

<210> SEQ ID NO 15
<211> LENGTH: 400
<212> TYPE: PRT
<213> ORGANISM: Mus musculus

<400> SEQUENCE: 15

His Ala Ser Gly Gly Met Gly Ala Gly Ala Ala Val Ala Ser Ala
 1               5                  10                  15

Gly Val Ile Tyr Pro Phe Gln Pro Arg Ala Arg Tyr Glu Asp Tyr Gly
                20                  25                  30

Gly Gly Gly Gly Glu Glu Gln Pro Glu Tyr Pro Ala Gln Gly Phe Tyr
            35                  40                  45

Pro Ala Pro Glu Arg Pro Tyr Val Pro Gln Pro Gln Pro Gln Pro Gln
 50                 55                  60

Pro Gln Pro Gln Pro Gln Pro Gln Pro Ser Asp Gly Leu Asp Arg Arg
65                  70                  75                  80

Tyr Ser His Ser Leu Tyr Asn Glu Gly Thr Pro Gly Phe Glu Gln Ala
                85                  90                  95

Tyr Pro Asp Pro Ser Thr Asp Val Ser Gln Ala Pro Ala Gly Ala Gly
            100                 105                 110

Gly Ile Tyr Gly Gly Ala Gly Asp Pro Arg Leu Gly Trp Tyr Pro Pro
        115                 120                 125

Tyr Ala Ala Asn Val Pro Pro Glu Ala Tyr Val Pro Pro Arg Ala Val
130                 135                 140

Glu Pro Gln Pro Pro Phe Arg Val Leu Glu Pro Pro Tyr Leu Pro Val
145                 150                 155                 160

Arg Ser Ser Asp Ala Pro Ser Gln Gly Gly Glu Arg Asn Gly Ala Gln
                165                 170                 175

Gln Gly Arg Leu Ser Val Gly Ser Val Tyr Arg Pro Asn Gln Asn Gly
            180                 185                 190

Arg Gly Leu Pro Asp Leu Val Pro Asp Pro Asn Tyr Val Gln Ala Ser
        195                 200                 205

Thr Tyr Val Gln Arg Ala His Leu Tyr Ser Leu Arg Cys Ala Ala Glu
210                 215                 220

Glu Lys Cys Leu Ala Ser Thr Ala Tyr Ala Pro Glu Ala Thr Asp Tyr
225                 230                 235                 240

Asp Leu Arg Val Leu Leu Arg Phe Pro Gln Arg Val Lys Asn Gln Gly
                245                 250                 255

Thr Ala Asp Phe Leu Pro Asn Arg Pro Arg His Thr Trp Glu Trp His
            260                 265                 270

Ser Cys His Gln His Tyr His Ser Met Asp Glu Phe Ser His Tyr Asp
        275                 280                 285

```
Leu Leu Asp Ala Ser Thr Gly Lys Lys Val Ala Glu Gly His Lys Ala
    290                 295                 300

Ser Phe Cys Leu Glu Asp Ser Thr Cys Asp Phe Gly Asn Leu Lys Arg
305                 310                 315                 320

Tyr Ala Cys Thr Ser His Thr Gln Gly Leu Ser Pro Gly Cys Tyr Asp
                325                 330                 335

Thr Tyr Asn Ala Asp Ile Asp Cys Gln Trp Ile Asp Ile Thr Asp Val
            340                 345                 350

Gln Pro Gly Asn Tyr Ile Leu Lys Val His Val Asn Pro Lys Tyr Ile
                355                 360                 365

Val Leu Glu Ser Asp Phe Thr Asn Asn Val Arg Cys Asn Ile His
    370                 375                 380

Tyr Thr Gly Arg Tyr Val Ser Thr Thr Asn Cys Lys Ile Val Gln Ser
385                 390                 395                 400

<210> SEQ ID NO 16
<211> LENGTH: 591
<212> TYPE: PRT
<213> ORGANISM: Bos taurus

<400> SEQUENCE: 16

Met Ala Leu Ala Leu Thr Gly Trp Gln Leu Val Trp Gly Ala Cys Val
1               5                   10                  15

Cys Val Leu Val His Gly Gln Gln Ala Pro Gly Gln Gly Ser Asp
            20                  25                  30

Pro Gly Arg Trp Arg Gln Leu Ile Gln Trp Glu Asn Asn Gly Gln Val
            35                  40                  45

Tyr Ser Leu Leu Asn Ser Gly Ala Glu Tyr Val Pro Pro Gly Pro Gln
    50                  55                  60

Gly Ser Glu Ala Asn Ser Arg Val Leu Leu Ala Gly Ala Pro Gln Ala
65                  70                  75                  80

Pro Pro Arg Arg Arg Gly Gly Leu Arg Arg Gln Ala Pro Ser Leu
                85                  90                  95

Pro Leu Pro Gly Arg Val Gly Ser Asp Thr Val Arg Gly Gln Ala Arg
            100                 105                 110

His Pro Phe Gly Phe Gly Gln Val Pro Asp Asn Trp Arg Glu Val Ala
            115                 120                 125

Val Gly Asp Ser Thr Gly Met Ala Arg Ala Arg Thr Ser Val Ser Gln
130                 135                 140

Gln Arg His Gly Gly Ser Ala Ser Ser Val Ser Ala Ser Ala Ser Ala
145                 150                 155                 160

Phe Ala Ser Thr Tyr Arg Gln Pro Ser Ser Phe Pro Gln Gln Phe
                165                 170                 175

Pro Tyr Pro Gln Ala Pro Phe Val Ser Gln Tyr Glu Thr Tyr Asp Pro
            180                 185                 190

Ser Thr Arg Thr Tyr Asp Gln Gly Tyr Val Tyr Arg Ser Ala Ser
    195                 200                 205

Gly Gly Leu Gly Ala Ala Val Ala Ser Ala Gly Val Val Tyr Pro
    210                 215                 220

Phe Gln Pro Arg Ala Arg Tyr Glu Glu Tyr Gly Gly Gly Gly Glu
225                 230                 235                 240

Glu Gln Pro Glu Tyr Pro Pro Gln Gly Phe Tyr Pro Ala Ala Pro Glu
                245                 250                 255

Arg Pro Tyr Ala Pro Gln Pro Ala Asp Gly Leu Asp Arg Arg Tyr Ser
                260                 265                 270
```

```
His Ser Leu Tyr His Glu Gly Thr Ala Gly Leu Glu Pro Ala Tyr Pro
        275                 280                 285
Asp Pro Gly Pro Asp Ala Ala Gln Pro Asn Gly Gly Gly Gly Gly Gly
        290                 295                 300
Thr Tyr Gly Gly Gly Gly Asp Pro Arg Leu Gly Trp Tyr Pro Pro
305                 310                 315                 320
Tyr Gly Asn Met Pro Pro Glu Ala Tyr Ser Pro Pro Arg Val Val Glu
                325                 330                 335
Pro Gln Pro Pro Phe Arg Val Leu Glu Pro Pro Tyr Leu Pro Val Arg
                340                 345                 350
Ser Ser Asp Ala Pro Pro Pro Gly Ser Glu Arg Asn Gly Ala Gln Gln
        355                 360                 365
Gly Arg Leu Ser Val Gly Ser Val Tyr Arg Pro Asn Gln Asn Gly Arg
        370                 375                 380
Gly Leu Pro Asp Leu Val Pro Asp Pro Asn Tyr Val Gln Ala Ser Thr
385                 390                 395                 400
Tyr Val Gln Arg Ala His Leu Tyr Ser Leu Arg Cys Ala Ala Glu Glu
                405                 410                 415
Lys Cys Leu Ala Ser Thr Ala Tyr Ala Pro Glu Ala Thr Asp Tyr Asp
                420                 425                 430
Val Arg Val Leu Leu Arg Phe Pro Gln Arg Val Lys Asn Gln Gly Thr
        435                 440                 445
Ala Asp Phe Leu Pro Asn Arg Pro Arg His Thr Trp Glu Trp His Ser
        450                 455                 460
Cys His Gln His Tyr His Ser Met Asp Glu Phe Ser His Tyr Asp Leu
465                 470                 475                 480
Leu Asp Ala Ala Thr Gly Lys Lys Val Ala Glu Gly His Lys Ala Ser
                485                 490                 495
Phe Cys Leu Glu Asp Ser Thr Cys Asp Phe Gly Asn Leu Lys Arg Tyr
                500                 505                 510
Ala Cys Thr Ser His Thr Gln Gly Leu Ser Pro Gly Cys Tyr Asp Thr
        515                 520                 525
Tyr Asn Ala Asp Ile Asp Cys Gln Trp Ile Asp Ile Thr Asp Val Gln
        530                 535                 540
Pro Gly Asn Tyr Ile Leu Lys Val His Val Asn Pro Lys Tyr Ile Val
545                 550                 555                 560
Leu Glu Ser Asp Phe Thr Asn Asn Val Val Arg Cys Asn Ile His Tyr
                565                 570                 575
Thr Gly Arg Tyr Val Ser Thr Thr Asn Cys Lys Ile Val Gln Ser
                580                 585                 590
```